United States Patent [19]
Ferguson

[11] Patent Number: 5,315,085
[45] Date of Patent: May 24, 1994

[54] OVEN THAT EXHIBITS BOTH SELF-RESISTIVE AND SELF-INDUCTIVE HEATING

[75] Inventor: Hugo S. Ferguson, Averill Park, N.Y.

[73] Assignee: Dynamic Systems Inc., Poestenkill, N.Y.

[21] Appl. No.: 987,368

[22] Filed: Dec. 7, 1992

Related U.S. Application Data

[63] Continuation-in-part of Ser. No. 645,190, Jan. 18, 1991, Pat. No. 5,202,542.

[51] Int. Cl.$^5$ .................. H05B 11/00; H05B 6/12; F27D 11/00
[52] U.S. Cl. .................. 219/50; 219/396; 219/407; 219/601; 219/634; 373/6
[58] Field of Search .............. 219/50, 10.493, 391, 219/396, 407, 390; 373/6; 99/DIG. 14, 483, 467

[56] References Cited

U.S. PATENT DOCUMENTS

| | | | |
|---|---|---|---|
| 458,163 | 8/1891 | Gutmann | 219/10.493 |
| 1,322,416 | 11/1919 | Fossati | 373/6 |
| 2,426,985 | 9/1947 | Darmara | 219/10.43 |
| 3,100,253 | 8/1963 | O'Connor | 219/50 |
| 3,632,944 | 1/1972 | Lease | 219/10.493 |
| 3,772,492 | 11/1973 | Brogden et al. | 219/10.79 |
| 3,790,735 | 2/1974 | Peters, Jr. | 219/10.493 |
| 4,109,128 | 8/1978 | Kohl | 219/10.79 |
| 4,627,259 | 12/1986 | Andersson et al. | 219/10.43 |
| 4,788,396 | 11/1988 | Mangein et al. | 219/10.43 |
| 4,820,892 | 4/1989 | Holmstrom et al. | 219/10.493 |
| 5,055,648 | 10/1991 | Iceland et al. | 219/10.47 |

FOREIGN PATENT DOCUMENTS

| | | | |
|---|---|---|---|
| 602111 | 7/1960 | Canada | 219/50 |
| 585825 | 10/1933 | Fed. Rep. of Germany | 374/46 |
| 1237322 | 6/1960 | France | 374/46 |
| 52-61844 | 5/1977 | Japan | 373/6 |
| 3-111517 | 5/1991 | Japan | 219/10.57 |
| 179998 | 7/1962 | Sweden | 219/50 |
| 675632 | 6/1976 | U.S.S.R. | |
| 873304 | 10/1981 | U.S.S.R. | 219/50 |
| 974208 | 11/1982 | U.S.S.R. | 374/51 |

Primary Examiner—Bruce A. Reynolds
Assistant Examiner—John A. Jeffery
Attorney, Agent, or Firm—Peter L. Michaelson

[57] ABSTRACT

An oven (1800) for use in conjunction with a dynamic thermal-mechanical testing system that exhibits both self-resistive and self-inductive heating whenever a sufficiently large alternating (AC) electrical current is passed through the oven. In one embodiment, the oven is fabricated from a material which undergoes self-resistive heating to radiantly heat an internal volume of the oven. The oven also includes appropriately shaped heating sections (1830), which undergoes self-resistive and self-inductive heating to compensate for heat losses into a support for the oven.

18 Claims, 13 Drawing Sheets

OVEN THAT EXHIBITS BOTH SELF-RESISTIVE AND SELF-INDUCTIVE HEATING

This application is a continuation-in-part of my co-pending United States patent application entitled "A Test Specimen/Jaw Assembly That Exhibits Both Self-Resistive and Self-Inductive Heating in Response to an Alternating Electrical Current Flowing Therethrough", filed Jan. 18, 1991 and accorded U.S. Ser. No. 07/645,190, and which has been assigned to the present assignee hereof.

BACKGROUND OF THE DISCLOSURE

1. Field of the Invention

The invention generally relates to dynamic thermal-mechanical testing systems, and more particularly to apparatus for use therein that provides both self-resistive and self-inductive heating whenever a sufficiently large alternating electrical current is passed therethrough, as well as to a self-resistively and self-inductively heated specimen to be tested therewith.

2. Description of the Prior Art

Metallic materials play an indispensable role as an essential component of an enormous number of different products. One crucial property of such materials is their ability to conduct electricity. Absent operation at superconductive temperatures, a metallic object possesses a resistance to electrical current flow based upon its cross-sectional size, length and resistivity. Owing to this resistance, the object will generate heat whenever an electric current is passed therethrough. This form of heating is the so-called "self-resistive heating". Self-resistive heating finds use in a wide number of diverse applications.

Different materials, including those that are metallic, possess widely varying mechanical, metallurgical and other properties. As such, the specific properties required of a material for use in a given application are first determined followed by selection of a specific material that exhibits appropriate minimum values of these properties. An essential step in selecting a specific material is first to determine its properties of interest by testing specimens of each such material being considered.

Materials are tested in a wide variety of different ways. One such way, which is experiencing substantially increasing use, is dynamic thermal-mechanical testing. Here, a specimen is gripped at each of its two ends in a jaw system. The specimen is typically in the form of a small cylinder or sheet section of a given material and has a substantially uniform circular, rectangular or square cross-sectional area. An electric current is serially passed from one jaw assembly to another and through the specimen to generate a rapid, but controlled, heating rate throughout the specimen. Simultaneously therewith, various measurements are made of the specimen. Depending upon the specific measurements being made, the specimen either may or may not undergo controlled deformation while it is being heated. If the specimen is to be deformed, then this deformation can be accomplished by moving one of the two jaw assemblies, at a controlled rate with respect to the other, in order to impart either a controlled tensile or compressive force to the specimen. Alternatively, the specimen can be controllably struck by one of the jaw assemblies in order to impart a forging force thereto while current is passing through the specimen to controllably heat it. Physical measurements, such as illustratively specimen dilation and temperature, are typically made while heating and deformation are simultaneously occurring. This testing not only reveals various static properties of the specimen material itself, such as its continuous heating transformation curve, but also various dynamic properties, such as illustratively hot stress vs. strain rates and hot ductility; the dynamic properties being particularly useful in quantifying the behavior of the material that will likely occur during rolling, forging, extrusion or other material forming and/or joining operations. One system that provides excellent dynamic thermal-mechanical testing is the GLEEBLE 1500 system manufactured by the Duffers Scientific, Inc. of Poestenkill, N.Y. (which also owns the registered trademark "GLEEBLE" and is the present assignee). This system advantageously heats the specimen self-resistively in order to generate transverse isothermal planes throughout the entire specimen. Specifically, since each specimen generally has a substantially uniform transverse cross-section throughout its length, then the current density will be uniform throughout the entire specimen which will cause uniform heating over the entire specimen cross-section.

The specimens used in dynamic thermal-mechanical testing usually fall within a fairly wide range of sizes. Tensile specimens are often cylindrical in shape and may be on the order of approximately 6 to 12 millimeters in diameter and approximately 10 to 20 centimeters in length. Tensile specimens having a rectangular cross-section are also used from time to time. Compression specimens also tend to be cylindrical in shape and may be on the order of approximately 8 to 15 millimeters in diameter and also approximately 10 to 20 millimeters in length. For simulating strip annealing, a suitable specimen will have a rectangular cross-section and may be on the order of approximately 1 millimeter thick and approximately 170 millimeters wide and approximately 300 millimeters long.

Regardless of the specific specimen that is to undergo dynamic thermal-mechanical testing, relatively high currents generally must be passed through the specimen in order to produce the requisite level of self-resistive heating therein. The amount of electrical current that is required to heat a specimen to a given temperature and/or at a given heating rate generally depends upon a number of factors, for example: the specific heat of the material; its resistivity; the geometric shape of the specimen, such as its cross-sectional area and length; heat loss from the specimen to its surroundings, principally including but not limited to the jaw system used to grip the specimen; and the value of the final temperature to be attained. In practice and owing to the low resistances of most specimens, generally only a few volts or less need to be applied across the specimen to conduct the required current therethrough.

As noted above, a specimen is securely held between two jaw assemblies within a dynamic thermal-mechanical testing system and specifically by a grip contained within each such assembly. A series path is established to route heating current from one jaw assembly through the specimen to the other jaw assembly. For several reasons, the grips and jaw assemblies must be substantially larger in size than the specimen itself. First, electrical connections must be made to opposite ends of the specimen to conduct the current required to heat the specimen but without causing an appreciable voltage drop across each jaw assembly. As such, the jaw assemblies must be sufficiently large to provide a very low resistance path for high levels of current flowing therethrough. Second, to prevent the jaw assemblies, particularly if they are not water-cooled, from adversely melting or softening during high temperature testing, the jaw assemblies must provide a sufficient mass so that for a given current level, the jaw assemblies will remain appreciably cooler than the specimen and will heat at a significantly lower rate. Third, mechanical loads, as noted above in the form of tensile, compressive or forging forces, are applied through the jaw assemblies to deform the specimen while it is heating. As such, the jaw assemblies must be of sufficient size to safely transmit these forces to the specimen without experiencing any deformation themselves.

A number of dynamic thermal-mechanical tests require that essentially no longitudinal thermal gradients exist along the mid-span of the specimen. However, in practice, thermal gradients often occur between the ends of the mid-span during heating. The reason for this stems from the fact that the jaw assemblies, being of considerably greater thermal mass than the specimen, tend to conduct considerable quantities of heat away from the ends of the specimen while that specimen is being self-resistively heated. This, in turn, causes the opposing ends of the specimen to be significantly cooler than its mid-span.

Either one of two well-known techniques is often used to remedy this heat loss; however, each of these techniques possesses one or more drawbacks which disadvantageously limits its utility. First, both jaw assemblies themselves can be heated to the specimen temperature to prevent heat from being conducted from the specimen to these assemblies. Not only does this technique require the addition of supplementary heating equipment to heat the jaw assemblies but also necessitates, along with the added cost of this equipment, that a substantial amount of energy be consumed to heat these assemblies. In addition, if the jaw assemblies are heated to a sufficiently high temperature, these assemblies may become too ductile and will themselves deform while mechanical forces are being applied therethrough to the specimen. Second, for a given current passing through the specimen, the temperature of each end of that specimen can be increased by appropriately reducing the cross-sectional area of the specimen material appearing at that end. While, this technique is very reproducible, it adversely limits the maximum rate at which the entire specimen can be heated. Specifically, this technique involves drilling a number of holes into each end of the specimen near its jaw contact area in order to reduce the amount of material present thereat. Inasmuch as the material is reduced at each end, the cross-sectional area of the specimen at that end is decreased which, in turn, locally increases the current density occurring thereat. For a given amount of current passing through the specimen, the increased current density in the ends locally increases the heating rate and the final temperature of each end. Unfortunately, to generate sufficient heat at the ends to adequately compensate for the heat being lost from the specimen to the grips, a sufficient amount of material must be removed from each end of the specimen which may adversely cause the heating rate thereat to rise too rapidly to the point where specimen material melts and burns off each end prior to the mid-span of the specimen attaining a desired final temperature. To prevent this effect, the self-resistive heating current must be appropriately reduced which, in turn, adversely reduces the rate at which the entire specimen can heat. For example, an adequate cross-sectional reduction may necessitate that the cross-sectional area of each end be reduced to approximately ¼ of its original value. However, to avoid excessive end temperatures from occurring in the specimen, the current that will pass through the specimen will need to be appropriately reduced such that the maximum heating rate of the entire specimen is only ¼ of the value that would otherwise be used if the specimen had a uniform cross-sectional area throughout. Unfortunately, limiting the heating rate in this fashion artificially limits the thermal behavior of the specimen that can be measured by the testing system. Furthermore, this technique also tends to decrease the mechanical strength of the specimen to the point where purely mechanical testing thereof (e.g. application of tensile, compressive or forging forces) may not be possible. Specifically, as material is removed from each end of the specimen, the mechanical strength of that end decreases below that of the mid-span which, during the application of an appropriate force is likely to cause the specimen to prematurely fail at its end(s).

Thus, a general need exists in the art for a technique for use in conjunction with, for example, a dynamic thermal-mechanical testing system that can compensate for conductive heat loss occurring from a specimen under test to the jaw assemblies without requiring the use of heated jaw assemblies and which does not appreciably limit the maximum rate at which the entire specimen can be heated or reduce the strength of a specimen to be used for purely mechanical testing.

In addition to metallic materials, ceramic and composite materials have begun to play an increasing role as essential components of an enormous number of different products. Ceramic and composite materials tend to have high strength, and many are capable of withstanding high temperature environments. However, typically these materials have poor ductility. As such, a ceramic or composite material can fracture when an extreme thermal gradient is established thereacross. For instance, if a thermal gradient is established across a ceramic or composite material specimen, such that one end of the specimen is maintained at a higher temperature than the other end of the specimen. The high temperature end of the specimen expands to an increased physical size when compared to the physical size of the other, i.e., cool, end of the specimen. As a result of this thermal gradient, the physical size of the specimen tends to transition from a larger, high temperature end to a smaller, low temperature end. This transition places a mechanical stress upon the specimen in the form of the larger end pulling apart the smaller end. An extreme thermal gradient can generate sufficient tensile forces to fracture the specimen. Additionally, ceramic and composite materials are susceptible to rapid changes in temperature known as thermal shock. As with extreme thermal gradients, thermal shock can fracture ceramic and composite specimens.

Presently, thermal testing of ceramic and composite materials is accomplished in conventional furnaces using induction or radiant heaters. Mechanical test apparatus, having jaws, which grip both ends of a specimen or anvils that compress both ends of a specimen, apply mechanical test forces while the furnace heats the specimen. To achieve a thermal gradient along the length of the specimen, multi-chamber furnaces are typically used. In such furnaces, a high temperature heating chamber heats one end of a specimen while a low temperature heating chamber heats another end. To accurately control the temperature in a mid-span region of the specimen, one or more intermediary heating chambers are positioned physically and thermally between the low and high temperature chambers. Consequently, the multi-chamber oven establishes a thermal gradient along the length of the specimen. However, multi-chamber furnaces tend to establish small, i.e., generally flat, thermal gradients that extend over relatively long specimen lengths. As such, multi-chamber furnaces are not capable of testing specimens in environments similar to those in which the materials operate, i.e., extreme thermal gradients.

Thus, a specified need exists in the art for a technique for use in conjunction with, for example, a dynamic thermal-mechanical testing system that can heat a ceramic or composite material specimen and which can generate steep thermal gradients along the length of the specimen.

SUMMARY OF THE INVENTION

My invention overcomes the deficiencies associated with techniques known in the art for remedying the conductive heat loss that occurs from the specimen ends to the jaw assemblies in, for example, a dynamic thermal-mechanical testing system. Through use of my invention, a specimen can be secured between grips in two opposing jaw assemblies and heated by an alternating (AC) electrical heating current passing serially through the jaw assemblies and my inventive heating apparatus but without establishing substantially any longitudinal thermal gradients either throughout the entire specimen or throughout its mid-span region. My inventive technique advantageously does not require the use of separately heated jaw assemblies and does not artificially limit the rate at which the entire specimen can be heated or reduce the strength of a specimen used for purely mechanical testing.

Specifically, in accordance with one aspect of my inventive teachings, appropriately shaped metallic conductors are placed in abutting electrical contact with the specimen ends and situated in the jaw assemblies such that the specimen ends are heated both self-resistively and self-inductively by the alternating (AC) heating current, at power line frequencies, that passes through the conductive specimen and the conductors. Alternatively, the ends of non-conductive specimens, such as ceramic specimens, can be heated by passing alternating heating current through conductors that support the ends of the specimens.

In one embodiment, a metallic conductor, with one or more appropriately shaped and sized self-resistive and self-inductive heating sections, is incorporated into each jaw assembly itself. A specimen is held in position by flat jaws or anvils. An end of this conductor abuts against and is in electrical contact with an opposing end-face of the specimen to provide good thermal and good electrical contact therebetween. This arrangement advantageously permits a desired longitudinal thermal gradient to be established end-to-end along the entire specimen. Similarly, to generate thermal gradients along a non-conductive specimen, a single metallic conductor, with one or more appropriately shaped self-resistive and self-inductive heating sections, is connected between each jaw assembly. In this regard, at least one portion of the conductor abuts against and is in thermal contact with an end of a non-conductive specimen. This alternative arrangement advantageously permits a desired longitudinal thermal gradient to be established end-to-end along the entire non-conductive specimen.

By incorporating appropriate heating sections within the jaw assemblies themselves, supplemental heat can be very easily introduced into each jaw assembly. While energy is consumed in heating each of these sections, the amount of this energy, while significant, is advantageously considerably smaller than that which would ordinarily be consumed if the jaw assemblies and/or specimen ends were to be heated using an additional source of energy.

In another embodiment, an oven is fabricated from a material in which a suitable amount of eddy currents can be induced by passing alternating current therethrough. The oven possesses a plurality of sidewalls which collectively form a cavity in which a specimen is coaxially positioned. The oven is further shaped, such as by appropriately bending its sidewalls, to possess illustratively two (or more) self-resistive and self-inductive heating sections in each sidewall. Each heating section is situated near an opposing end of the oven. Each such section is formed to illustratively have two adjacent, though non-abutting, serially connected legs. The legs in each section form illustratively a "hat" or inverted "U" shape, though triangular and other shapes could also be used. Within each section, the current that flows through each leg induces eddy current flow in the other leg which inductively heats the latter. Inasmuch as current flows in an opposite direction in each leg in a section with respect to current flow through the other leg therein, both legs in that section self-inductively heat. The resulting self-inductive heat, as well as the self-resistive heat, produced in both legs adds to the self-resistive heat generated in the oven sidewalls by the current flowing therethrough. The amount of heat that is inductively generated is governed by the size and shape of each section, including the length of each leg as well as the distance between the legs. By choosing the appropriate size and shape of each section, the amount of additional heat generated through self-induction can advantageously compensate for any heat that is conducted from the oven ends into both jaw assemblies. This, in turn, permits a uniform temperature, without substantially any longitudinal temperature gradients, to be established end-to-end throughout the mid-span of the oven by an alternating current passing therethrough. Consequently, the cavity defined by the oven sidewalls is maintained at a uniform temperature. As such, a specimen within the oven will correspondingly heat uniformly.

An important feature of the oven is that access to the cavity is generally provided via open end of the oven. As such, a supporting mechanism, such as jaws, anvils, or extension shafts of a mechanical testing system positions the specimen coaxially with a longitudinal axis of the oven. The supporting mechanism generates mechanical stress, such as compression, torsion, and/or tension, upon the specimen independent of the heating by the oven. Consequently, the inventive oven can be used in conjunction with a conventional mechanical testing system to perform mechanical testing at elevated temperatures. Additionally, by altering the size and shape of the self-inductive/self-resistive heating sections, the oven accurately generates desired thermal gradients in the inner volume and along the specimen.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate highly similar or identical elements that are common to various figures.

DETAILED DESCRIPTION

After considering the following description, those skilled in the art will clearly realize that the broad teachings of my invention can be readily utilized in conjunction with nearly any self-resistively heated material, in which a suitable amount of eddy currents can be induced therein, in order to increase the amount of heat generated in that material beyond that obtainable through only self-resistive heating. In essence, a material formed in accordance with my invention generates both self-resistive and self-inductive heat from a single common source of alternating (AC) heating current passing through the specimen. The teachings of my invention are also applicable to heating both conductive and non-conductive material specimens through specially constructed self-resistive and self-inductive jaw assemblies in a thermal-mechanical materials testing system. Additionally, the teachings of my invention can be used to produce an oven capable of heating both conductive and non-conductive material specimens. For purposes of illustration and to simplify the following discussion, I will specifically describe my invention in the context of use with specimens of typical conductive and non-conductive materials that can be tested with a dynamic thermal-mechanical materials testing system, such as illustratively the GLEEBLE 1500 and the GLEEBLE 2000 systems manufactured by the Duffers Scientific, Inc. of Poestenkill, N.Y. (which also owns the registered trademark "GLEEBLE" and is the present assignee) and with various jaw assemblies and ovens that can be used in such systems.

Figure 1:
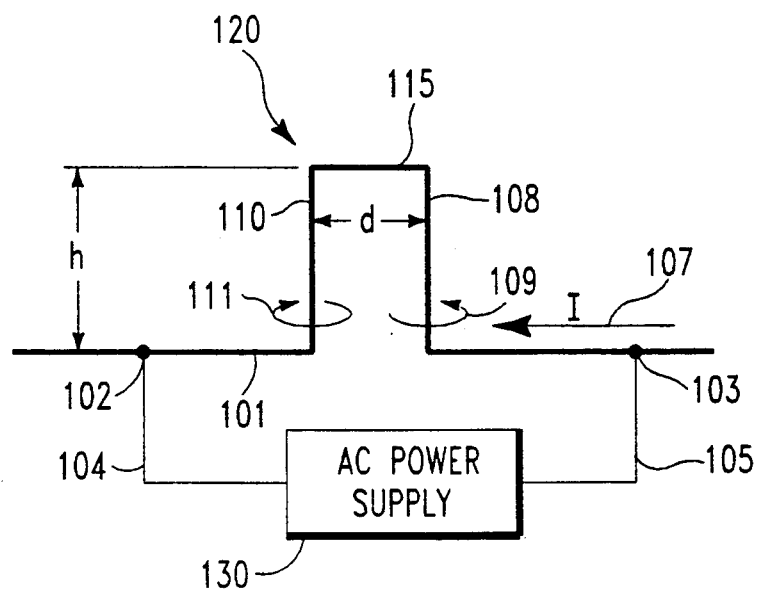
FIG. 1 shows a simplified schematic diagram of a piece of material, illustratively a wire, appropriately formed which undergoes both self-resistive and self-inductive heating by virtue of a single alternating (AC) current (I) flowing therethrough.

To facilitate reader understanding, FIG. 1 shows a simplified schematic diagram of a piece of material which is formed in conjunction with my inventive teachings and that undergoes both self-resistive and self-inductive heating by virtue of The magnetic flux lines generated by leg 108 penetrate leg 110 and cause eddy currents to flow therein. Similarly, the magnetic flux lines generated by leg 110 penetrate leg 108 and cause eddy currents to flow therein. These eddy currents, formed by inductive coupling between the two legs, also generate heat, hereinafter referred to as "self-inductive heat", due to the resistance of the material in each leg through which these eddy currents flow. The magnitude of the eddy currents depends upon the strength of the magnetic field generated by each leg in section 120 and the amount of that field which penetrates into the other leg situated in that section. Either reducing the inter-leg spacing d between the vertical risers or increasing the length h of each such riser will increase the magnetic coupling between the risers, the eddy currents induced therein and hence the amount of self-inductive heat generated thereby.

Through this arrangement, the total amount of heat generated in wire 101 is the sum of the self-resistive heat and the self-inductive heat. Inasmuch as both sources of heat are generated by the same current (I), this arrangement permits more heat to be generated in the wire than that which would result from self-resistive heating alone, i.e. the heat that would result in the wire if section 120 were to be replaced by a straight length of wire.

Figure 2:
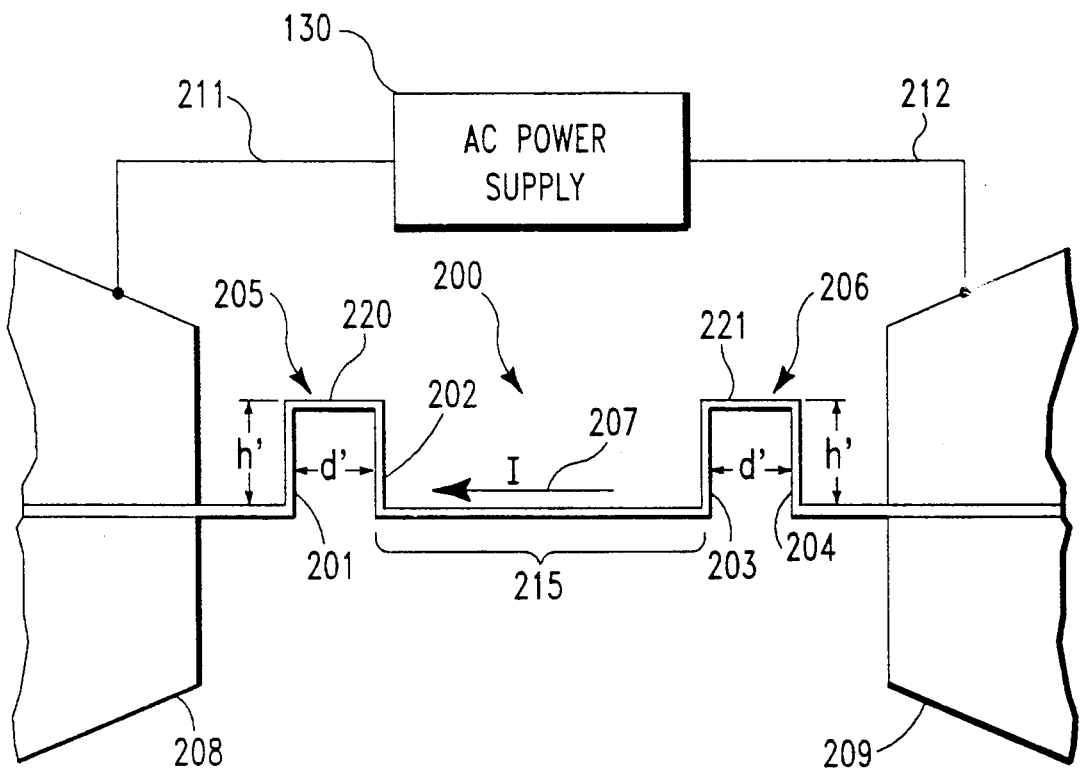
FIG. 2 shows a simplified diagram of an embodiment of a test specimen, formed in accordance with my inventive teachings, which is held between two jaw assemblies of a dynamic thermal-mechanical testing system and that experiences both self-resistive and self-inductive heating.

With the above in mind, FIG. 2 shows a simplified diagram of an embodiment of test specimen 200 formed in accordance with my inventive teachings which is held between two jaw assemblies 208 and 209 of a dynamic thermal-mechanical testing system and that experiences both self-resistive and an alternating (AC) current (I) flowing therethrough. Here, the conductive material, illustratively wire 101, has a uniform transverse cross-sectional area and a constant electrical resistance per unit length. Furthermore, the material is one in which a suitable amount of eddy currents can be induced by an external magnetic field. Wire 101 is serially connected at points 102 and 103 and, via respective leads 104 and 105, to power supply 130. This supply provides a source of low voltage high current alteracting (AC) power at power line (e.g. 50 or 60 Hz) frequencies. For one half-cycle of applied power, current (I) flows through material 101 in the direction shown by arrow 107; during the next half-cycle, the direction of current flow is reversed from that shown. Owing to the uniform resistance/unit length of wire 101, this current will establish a constant self-resistive heating rate along the length of the wire between points 102 and 103. As such, each incremental length of the wire will generate the same amount of self-resistive heat.

As shown, wire 101 is fabricated to contain heating section 120 formed of opposing legs (illustratively shown as vertical risers) 108 and 110, having height h and separation d, connected by transverse leg 115 of length d. The three legs in this section form illustratively a "hat" or inverted "U" shape. With this arrangement, current flowing in the direction indicated by arrow 107 generates circular lines of magnetic flux in the directions indicated by arrows 109 and 111 around legs 108 and 110, respectively. Similar lines of flux, though reversed in direction, are generated by the current as it flows in the direction opposite to that shown by arrow 107. self-inductive heating. Here, specimen 200, shown in longitudinal cross-section, is illustratively a strip annealing test specimen through which alternating current (I) at power line frequencies will be passed according to a pre-determined test schedule to heat treat the specimen in a manner that simulates a desired strip annealing production process. Specimen 200, which has a transverse rectangular cross-section, contains two heating sections 205 and 206 separated by mid-span region 215. The mid-span region typically has a length of approximately 200 millimeters. The entire specimen has a uniform width typically on the order of 150 millimeters and a uniform thickness ranging between approximately 0.25 to 1.5 millimeters depending upon the specific annealing process being simulated.

As shown, power supply 130 is connected, through leads 211 and 212, to jaw assemblies 208 and 209, respectively. These assemblies, which are highly conductive, collectively grip specimen 200 at opposing contact regions thereon and provide electrical connections for longitudinal current flow through the specimen. During one half-cycle of applied AC power, current flows through the specimen in the direction shown by arrow 207, and reverses its flow during the next half-cycle thereof. Heating sections 205 and 206 are formed of two opposing legs (also illustratively shown as vertical risers) 201 and 202, and 203 and 204, connected by transverse legs 220 and 221, respectively. The opposing legs in each section have the same height h' and are separated by the same spacing d'. Each of these sections generates heat in the same manner as discussed above. As such, the current flow through specimen 200 induces eddy current flow within sections 205 and 206 and provides self-inductive heat in legs 201, 202, 203 and 204 which, in turn, raises the temperature of these legs in excess of that which would occur therein through self-resistive heating alone. Consequently, if the jaws assemblies and the mid-span region are at lower temperatures than these legs, then a portion of the heat generated in these legs flows through specimen 200 to jaw assemblies 208 and 209; another portion flows into mid-span region 215.

By properly sizing and shaping each of the heating sections 205 and 206, both the self-inductive and self-resistive heat generated therein can substantially, if not totally, compensate for the entire self-resistive heat loss that occurs from the specimen into the jaw assemblies and thereby permit a substantially uniform heating rate to occur entirely throughout mid-span region 215 without substantially any longitudinal temperature gradients appearing therein. By increasing or decreasing the spacing $d'$ between or the height $h'$ of each vertical riser, the amount of self-inductive heat that can be generated in each section, for a given current flow, can be correspondingly changed. For example, increasing the height $h'$ or decreasing the spacing $d'$ will increase the self-inductive heat. Illustratively, for a steel specimen having a thickness of 1 millimeter, the height $h'$ of vertical risers 201, 202, 203 and 204 can each be 12 millimeters with the spacing $d'$ between two adjacent risers also being 12 millimeters. Ideally, to prevent excessive temperatures from appearing in the specimen material situated near the ends of mid-span region 215 and, as a result, establishing essentially no longitudinal temperature gradients in the mid-span region, the size and shape of the legs in each heating section should be set such that the self-inductive and self-resistive heat generated thereby matches the heat losses occurring from the specimen to jaw assemblies 208 and 209. Once the legs are so set, then during subsequent heating, the temperature of the heating sections will substantially, if not precisely, equal and track the temperature occurring at the middle of specimen 200 thereby producing essentially no thermal gradients occurring along mid-span region 215 in the specimen. Alternatively, if desired, the size and shape of each heating section can be suitably adjusted to permit a longitudinal thermal gradient to appear in the mid-span region which increases towards the center of the mid-span region or decreases therefrom. Moreover, in order to establish a desired longitudinal temperature gradient throughout the mid-span region, a testing specimen, fabricated in accordance with my inventive teachings, can even contain heating sections that have unequal sizes and/or different shapes. Inasmuch as each heating section is mechanically established thereby subject to excellent dimensional control and the heating current flowing through the specimen can be readily controlled quite precisely, nearly any desired thermal gradient can not only be easily and accurately generated throughout the entire mid-span region of the testing specimen but is also accurately reproducible.

To assure that sufficient heating occurs within sections 205 and 206, specimen 200 must possess the ability to generate self-resistance heat and have a sufficient amount of eddy currents induced therein. Specifically, eddy currents, which inductively heat a material, result from changing magnetic flux lines that penetrate into that material. Various factors govern the amount of inductive heating that can occur; namely, inter alia, the magnetic properties of the material itself, such as its magnetic permeability as well as its magnetic path length and shape; the field strength available to induce eddy current flow in the material; and the electrical resistance of the material (to usually circular eddy current flow therein). Materials of higher resistance will generate more inductive heat from a given level of eddy current flow than materials having lower resistance; however, larger eddy current flow can be established in such lower resistance materials for a given field strength. The magnetic permeability of ferromagnetic materials is relatively high, such as several thousand, which, in turn, permits these materials to exhibit increased self-inductive heating over paramagnetic or diamagnetic materials, i.e., materials that respectively have a magnetic permeability slightly larger than or less than one. However, as a ferromagnetic material is heated above its so-called and well-known "Curie temperature", i.e. the temperature at which that material becomes paramagnetic and its permeability decreases to slightly above one, its induced field strength decreases as does the self-inductive heating generated therein. I have experimentally found that although the resulting self-inductive heat that is generated by a ferromagnetic material is less whenever that material is heated above its Curie temperature than that which results whenever that material remains below this temperature, the resulting decrease is modest. This indicates that the effect of the shape and size of each heating section, particularly on the magnetic coupling therein and the eddy currents flowing thereby, is more predominant than the amount of heat generated in each section through ferromagnetic effects.

Figure 4:
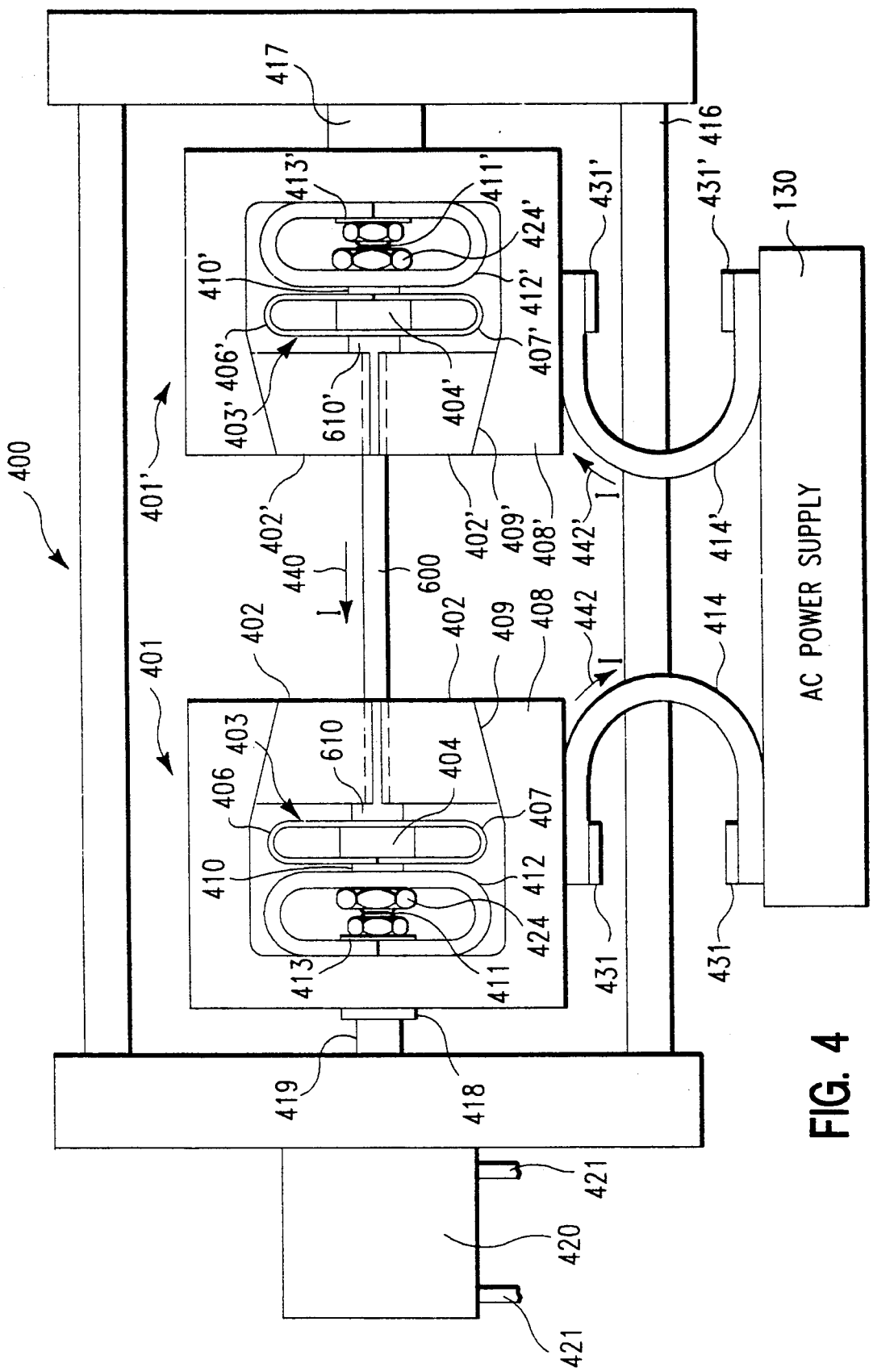
FIG. 4 shows a detailed plan view of a tension/compression test apparatus which forms a portion of the dynamic thermal-mechanical testing system and that incorporates jaw assemblies fabricated in accordance with my inventive teachings.

Furthermore, as the frequency (particularly the rate of change) of the external magnetic field increases, the amount of self-inductive heat that will be generated in the material also increases. However, as a result of well-known "skin effects", these eddy currents will penetrate less deeply into the material as the frequency of the field increases. As such, typical induction heating applications rely on using heating currents with frequencies up to approximately 500 kHz. At power line frequencies, the external magnetic field will fully penetrate the material, even a relatively thick cross-section thereof, though the amount of inductive heat that will be generated thereby is relatively small as contrasted to that which will occur at higher frequencies. Nevertheless, I have experimentally found that the amount of self-inductively and self-resistively generated heat produced in even relatively small sized heating sections, such as sections 205 and 206, when power line frequency heating currents are used is more than adequate to compensate for heat loss that occurs to the jaw assemblies, such as assemblies 208 and 209. Since the affect of ferromagnetism does not markedly change the amount of self-inductive heat that is generated at typical test temperatures, specimen 200 (as well as conductors 403 and 403' shown in FIG. 4, 503 shown in FIG. 5, and 803 and 803' shown in FIG. 8—all of which are discussed in detail below), can be readily fabricated from suitable ferrous or non-ferrous materials.

Jaw assemblies 208 and 209 may be water cooled to maintain a relatively low jaw temperature or allowed to increase in temperature; the latter merely relying on non-forced air cooling. Inasmuch as the heat loss that occurs to water cooled jaw assemblies will be substantially higher than that which occurs to non-forced air cooled jaw assemblies, the shape and size of heating sections 205 and 206 will need to be adjusted to generate more self-inductive heat for specimens being gripped by water cooled jaw assemblies than for non-forced air cooled jaw assemblies in order to properly offset the heat loss that occurs to the water cooled jaw assemblies.

Figure 3:
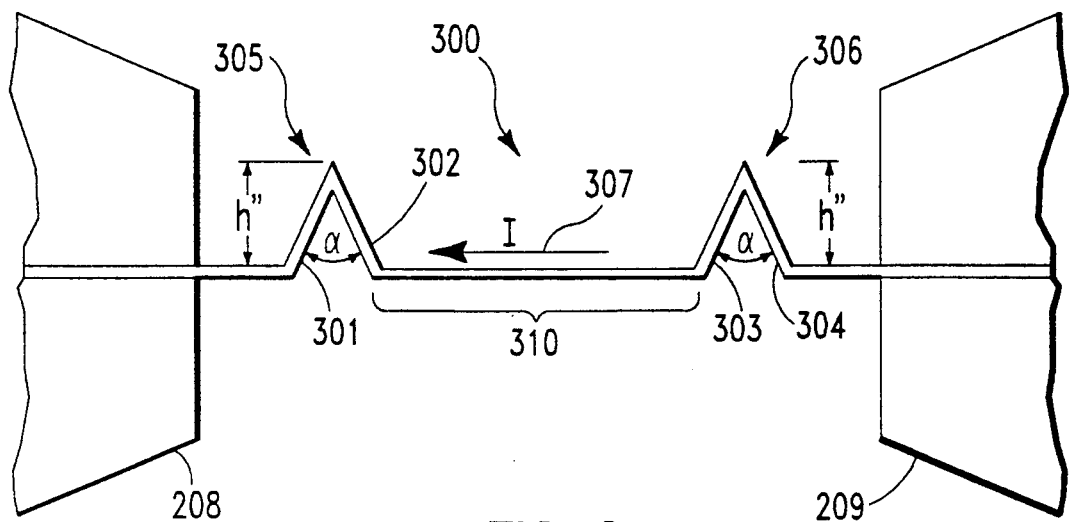
FIG. 3 shows a simplified diagram of an alternate embodiment of a test specimen formed in accordance with my inventive teachings which is also held between two jaw assemblies of a dynamic thermal-mechanical testing system and that also experiences both self-resistive and self-inductive heating.

Clearly, the specimen can be fabricated to use other non-rectangular shapes for each heating section. Inasmuch as the amount of self-inductive heat required in most sheet metal specimens tends to be relatively small, a variety of non-rectangular shaped heating sections can be used. In this regard, FIG. 3 shows a simplified diagram of an alternate embodiment of a test specimen, here having triangularly-shaped heating sections, formed in accordance with my inventive teachings which is also held between two jaw assemblies of a dynamic thermal-mechanical testing system and that also experiences both self-resistive and self-inductive heating. As shown, jaw assemblies 208 and 209 grip test specimen 300 which contains triangularly-shaped heating sections 305 and 306 separated by mid-span region 310. Here, sections 305 and 306 are formed by intersecting legs 301 and 302, and 303 and 304, respectively, which subtend a pre-defined angle, $\alpha$, therebetween. As this angle is increased or both legs in a section are shortened, the amount of magnetic induction and self-inductive heating that is produced in each such leg will correspondingly decrease. Correlatively, smaller angles or lengthened legs will tend to increase the amount of magnetic induction and self-inductive heating produced in each section. As an example, if specimen 300 has a thickness of 1 millimeter, then legs 301, 302, 303 and 304 that form sections 305 and 306 may each be approximately 11 millimeters in length with the height, $h''$, of each section being approximately 5 millimeters. As a consequence of these dimensions, each section will heat more rapidly than mid-span region 310 with excess heat flowing from that section both into the mid-span region and into the nearby jaw assembly. Illustratively, if sufficient current is applied to specimen 300 to generate a heating rate of 20° Centigrade/second (C./sec.) in mid-span region 310, then sections 305 and 306 will heat somewhat faster than the mid-span region. If sufficient current is used to generate a heating rate of 40° C./sec. in the mid-span region, then the temperature of the mid-span region will considerably lag that of both heating sections. Specifically, after passing current through specimen 300, with the sizes set forth above, to heat the center of the mid-span region at a rate of 40° C./sec to a temperature of 800° C., both heating sections 305 and 306 may be approximately 100° C. warmer than the center of mid-span region 310. The size and shape of sections 305 and 306 would normally be set to minimize over temperature at the specimen ends for the chosen heating rate and to account for specimen cross-section, type of material, maximum temperature and specimen mid-span length in order to provide essentially no longitudinal temperature gradient throughout the mid-span of the specimen.

Forming such a triangular shape for each heating section advantageously requires one less bend grips were used within jaw assemblies 208 and 209 to assure a substantially uniform gripping force along the entire width of the specimen. During testing, the jaw assemblies, including the wedge grips, were also water-cooled to remain at room temperature. Separate thermocouples were spot welded to each specimen 35 millimeters inward of each jaw contact area—one of which was situated slightly inward of the heating section—and also at the center of the mid-span region. The output of each thermocouple was periodically sampled by the GLEEBLE 1500 system throughout a test interval defined by the heating schedule. Inasmuch as carbon steel has a higher conductivity than stainless steel, one would expect that it would tend to be somewhat more difficult to appropriately size the heating sections in a carbon steel specimen in order to maintain relatively small thermal gradients over a relatively long specimen. The measured test data confirmed this. Furthermore, since stainless steel has a relatively high resistance, the air flow around such specimens needs to be restricted in order to prevent surface cooling. As such, each stainless steel specimen was covered with a ceramic blanket during testing. Vacuum testing could alternately be used and would generate the same test results. Based upon measured data, the temperatures of the stainless steel and aluminum specimens at both the heating section and the mid-span region tracked each other with no appreciable differences occurring therebetween during the entire test interval for heating at either 5 or 50° C./second. As expected and due to conductive heat losses that occurred from the ends of the specimen to the respective jaw assemblies, the temperature of the specimen end located opposite to that situated near the heating section tended to remain significantly cooler than that measured at the other two locations thereon. Similar results occurred in the carbon steel specimens though with a somewhat increased variation occurring between the temperatures at the center of the mid-span region and the heating section during the holding and cooling intervals. For specimens heated at 5° C./second, the maximum variation amounted to approximately 50° C.; while for specimens heated at 50° C./second, the maximum variation amounted to approximately 30° C. It is expected that these small variations could be removed by appropriately modifying the size of the heating sections in the carbon steel specimens.

Test specimens similar in shape to those described above may have a relatively large cross-sectional area or a relatively short mid-span region. Examples of such specimens include round and square bars up to and exceeding 20 millimeters in diameter or per side. When such large specimens are mechanically tested, not only must the electrical connections to these specimens be sufficiently large and strong to carry the requisite heating current but the mechanical connections, through the jaw assemblies, to both ends of the specimen must be adequate to control and maintain and accurately transmit the forces required for compressive and/or tensile testing to the specimen. Furthermore, when specimens are tested at uniform temperatures, it is a common well-known standard ASTM (American Society for Testing and Materials) practice in the art to slightly reduce the cross-sectional area of the mid-span region of the specimen in order to induce fracturing to occur therein. In specimens that have a circular cross-sectional area, this reduction is readily accomplished by reducing the diameter of the specimen along a relatively large radius starting with a zero percentage reduction at an inward end of each jaw contact region and extending inward with gradually increasing reductions until a 1% reduction occurs at the center of the mid-span region of the specimen.

Furthermore, each jaw assembly can include appropriate conductors that are shaped to provide the necessary self-inductive and self-resistive heating in order to establish a desired longitudinal thermal gradient end-to-end along the entire specimen. In this case, the testing specimen can have a substantially uniform cross-section. In this regard, FIG. 4 shows a detailed plan view of a tension/compression test apparatus which forms a portion of the dynamic thermal-mechanical testing system and that incorporates jaw assemblies fabricated in accordance with my inventive teachings.

As shown, specimen 600 is held between two jaw assemblies 401 and 401', both of which are identical, mounted in load frame 416. Jaw assembly 401' is stationary; while piston rod 419 of hydraulic cylinder 420 moves jaw assembly 401 laterally so as to impart a desired tensile/compressive force to the specimen. Hydraulic ports 421 connect the cylinder to a suitable servo controlled hydraulic system (well known and not shown) to accurately control the relative movement between the jaw assemblies and hence the tensile and compressive forces imparted to specimen 600. Load cell 417 connects stationary jaw assembly 401' to the load frame. This load cell accommodates relatively little movement, typically on the order of 0.1 mm, for a full load. Flexible leads 414 and 414' connect both jaw assemblies to high current AC power supply 130 in order to route heating current from the supply serially through both the jaw assemblies and the specimen. Fasteners (typically bolts) 431 and 431' secure these leads to both jaw assemblies and appropriate output terminals of the power supply. In operation and during one-half cycle of applied AC power, heating current (I) flows in the directions shown by arrows 442', 440 and 442; while, during the next successive half-cycle, the heating current reverses its direction. To prevent current from flowing into hydraulic cylinder 420, insulating disk 418 is situated between and abuts against both moveable jaw assembly 401 and one end of piston rod 419.

Figure 6:
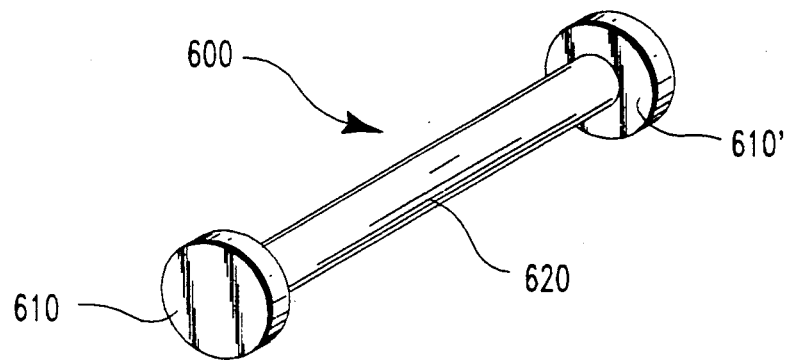
FIG. 6 shows an illustrative "button-end" cylindrical test specimen, having a circular cross-section, that can be used in conjunction with my inventive jaw assemblies shown in either FIGS. 4 or 5.

Specimen 600, also shown in FIG. 6, has two buttons 610 and 610' of substantially equal cross-sectional area machined on opposing ends thereof. Between these buttons, the specimen has a substantially uniform transverse cross-sectional area. Alternatively, each opposing end of specimen 600 may be threaded with a nut being appropriately used to restrain the specimen within each jaw assembly. Jaw assemblies 401 and 401', shown in FIG. 4, respectively contain wedge grip pairs 402 and 402' which are fabricated from a high strength insulating material, including any one of a variety of well known ceramic or composite materials, and are retained within jaw bodies 408 and 408'. Both jaw bodies are fabricated from any one of several well known materials that will withstand, at the maximum test temperature, the high forces used in mechanically deforming the specimen. These jaw assemblies may be water-cooled, if desired. Jaw bodies 408 and 408' have a wedge pocket with taper sections 409 and 409', respectively, that each has a taper matching on a complementary basis the outer taper on each of the wedge grips. This taper is approximately 10 degrees as measured to a longitudinal axis of the specimen. Each of the wedge grips has a machined groove along its inner contour that accurately fits the outer peripheral contour of the specimen. The wedge grip pairs are situated on specimen, as shown, such that the grip contact area on the specimen is located inward of each button. Wedge grip pairs 402 and 402' (as well as wedge grips 509 and 509' shown in FIG. 5) may also be pneumatically operated in order to provide a uniform gripping force along a relatively wide specimen fabricated from sheet stock. As depicted in FIG. 4, conductors 403 and 403', each being preferably a strip shaped to resemble a "U" or an elongated oval (as shown), abut against each end-face of the specimen. Blocks 404 and 404', made of a suitably high strength insulating material—typically any one of many well known ceramic materials, are placed within the conductors both to prevent their deformation during compressive testing and to force current flow completely through these conductors. The materials used for these blocks is selected, based upon the expected stress level therein and the maximum test temperature, from any one of several well known materials such that during compression testing, the thickness of these blocks and the overall width of each conductor can be minimized. Alternatively, the so-called "best available" materials can be used for all tests, though such materials may be prohibitively costly. Once the appropriate material has been selected, then the compression strain on the combined thickness of conductors 403 and 403' (two wall thicknesses in each as shown) and the corresponding block will substantially remain at its lowest point.

Conductors 403 and 403' form the heating sections and hence provide both self-inductive and self-resistive heating in the manner described in detail above. These conductors are appropriately sized and shaped to impart a requisite amount of heat into both end-faces of specimen 600 that offsets the heat losses that occur from the specimen into both jaw assemblies thereby assuring that substantially no longitudinal thermal gradients appear along the entire specimen during heating. Based upon the amount of self-inductive and self-resistive heat desired, conductors 403 and 403' may each have one or two U-shaped heating sections. If each of these conductors is formed to have two such sections 406 and 407, or 406' and 407' (as shown), then each such section should have approximately the same shape and cross-sectional area so that it will carry approximately one-half of the total current flowing through the specimen. If specimen 600 is low carbon steel and approximately 10 millimeters in diameter thereby providing a cross-sectional area of approximately 78.5 square millimeters and conductors 403 and 403' are each fabricated from 2 millimeter thick sheet stock that has substantially the same electrical and thermal resistivity as the specimen, then the width of the conductor used to form each heating section 406, 407, 406' and 407' will be approximately 19.6 millimeters. Alternatively, if each sheet stock based conductor were to have only one heating section, then the cross-section of this section should approximately match that of the low carbon steel specimen—the thickness of the conductor would either be twice as thick as that used to fabricate sections 406, 407, 406' and 407' or lessened but with the latter requiring an increase in the width of the conductor.

The thickness of blocks 404 and 404' determines the spacing between the vertical legs of each heating section and hence determines the degree of magnetic coupling therebetween and self-inductive heat that will be generated therein. Each of these conductors may be shaped from a flat piece of material that has been formed to have two opposing symmetric 180 degree bends that produce two corresponding heating sections. The interface between each of conductors 403 and 403' and a corresponding end-face of specimen 600 should preferably be only a mechanical butt joint without any other type of connection. Not only will each of the conductors heat an end of the specimen but advantageously these conductors will also thermally isolate that end from the mechanical/jacking components, which will soon be described, as well as from the other high current conductors.

As noted above, the material used to form each of conductors 403 and 403' can be any one of many well known conductive ferrous or non-ferrous materials, as discussed above, which can undergo self-resistive heating and in which a suitable amount of eddy currents can be induced, with the specific material being selected based on its high temperature strength and the mechanical compressive force that will be involved in testing the specimen, the type of specimen being tested, the anticipated current level, the maximum test temperature and the expected time at that temperature. If testing is to occur up to approximately 1000° C., then conductors 403 and 403' can each be fabricated from type 304 austenitic stainless steel. Other materials, such as INCONEL type 718 alloy or RENÉ type 95 nickel-based alloys may also be used for these conductors (INCONEL and RENÉ are trademarks of International Nickel Company and General Electric Company, respectively) particularly since their high temperature properties surpass those of austenitic stainless steels. In those situations where specimen 600 may exhibit a tendency to stick to conductors 403 and 403', a thin sheet (not specifically shown), typically between 0.1–0.25 millimeter, of an appropriate material, such as carbon or tantalum, may be placed between each end-face of the specimen and each abutting conductor. Such a sheet, which prevents welding, would likely reduce any such sticking which would otherwise occur between the specimen end-face and the conductor surface as the specimen is being crushed during compression testing and arising from high temperature at the button, high force, possible diffusion bonding thereat and/or welding. Such a sheet can also be similarly and advantageously used with the jaw assemblies shown in FIGS. 5 or 8, both of which are discussed in detail below.

Conductors 403 and 403' abut against conductive washers 410 and 410' which, in turn, abut against high current bands 412 and 412', respectively. These washers provide a uniform contact area between the conductors and the bands. The combination of conductors 403 and 403' and blocks 404 and 404' are respectively compressed through washers 410 and 410' by corresponding screw jacks 411 and 411' so as to assure a tight abutting mechanical and serial electrical connection among the bands, washers and conductors. The screw jacks expand the overall width of bands 412 and 412'. Each band may be fabricated using a number of laminations of copper strip in order to provide flexibility and handle high currents without generating much heat therefrom. To prevent current from flowing through screw jacks 411 and 411', these jacks are insulated from bands 412 and 412' by corresponding insulating disks 413 and 413'.

Inasmuch as high current bands 412 and 412' are typically formed of copper and are in contact, through washers 410 and 410', with conductors 403 and 403' which produce self-inductive and self-resistive heat, these bands should be water-cooled to limit their temperature. This may be readily accomplished by water cooling jack nuts 424 and 424' which respectively contact bands 412 and 412'. Alternatively, a separate water-cooled "chill" block having good thermal conductivity may be inserted between each jacks and an interior surface of the corresponding band. In either case, the longevity of the life of the bands will be adversely shortened if these bands are not properly cooled during high current testing.

Figure 5:
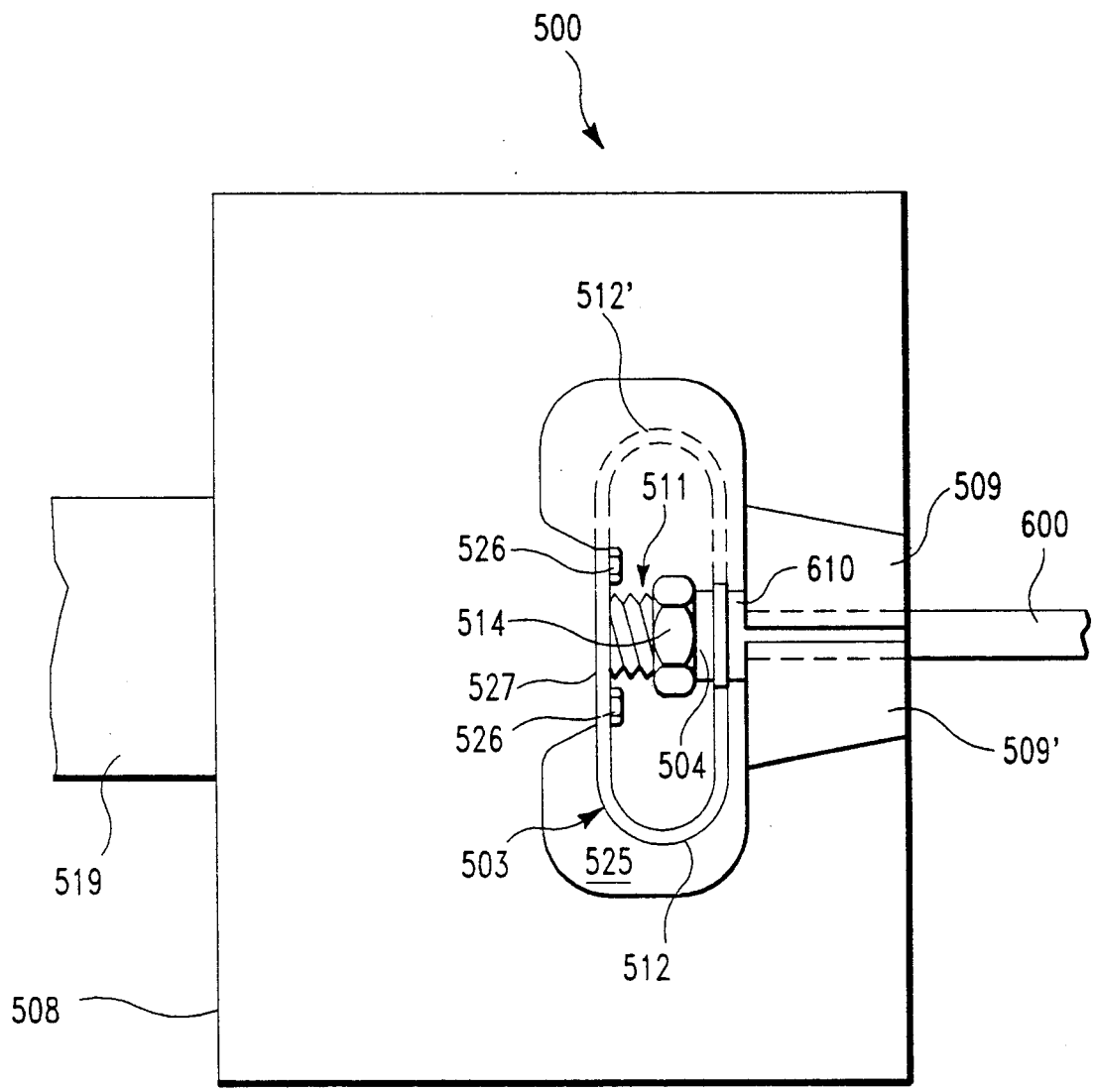
FIG. 5 shows an alternative and simplified embodiment of my inventive jaw assembly that can be used in the tension/compression test apparatus shown in FIG. 4.

FIG. 5 shows an alternate and simplified embodiment of my inventive jaw assembly that can be used in the tension/compression apparatus shown in FIG. 4. Inasmuch as an identical jaw assembly is secured to the opposing side of specimen 600, partially shown in FIG. 5, then to simplify the drawing, only jaw assembly 500 is depicted in this figure and will be specifically described below.

Body 508 of jaw assembly 500 can be fabricated from austenitic stainless steel or high strength aluminum, neither of which is ferromagnetic. Certainly, other materials can be used for body 508, but any other such material should not be ferromagnetic in order to maximize the electrical performance of the jaw assembly, specifically the amount of self-inductive heat that is generated in conductive band 503 and imparted to the specimen end. Pocket 525 is machined into jaw body 508 and runs completely transversely through the jaw body, i.e., in a direction perpendicular to the plane of the figure. Similar to jaw assemblies 401 and 401' shown in FIG. 4 and described in detail above, pocket 525 shown in FIG. 5 includes a wedge pocket with 10 degree taper sections oriented with respect to a longitudinal axis of the specimen. A pair of wedge grips 509 and 509', each having an external taper that matches that of the wedge pocket, abuts against opposing sides of this pocket. Here too, wedge grips 509 and 509' mutually grasp the specimen such that the grip contact area on the specimen is located inward of button 610. Each wedge grip has an internal contour that accurately matches the outer peripheral contour of specimen 600: round for specimens having a circular cross-section and flat for sheet specimens having a rectangular or square cross-section.

Wedge grips 509 and 509' are fabricated from a high strength insulating material. As noted above, this material may be a ceramic or composite material that provides good thermal and good electrical insulation. These wedge grips, as well as those shown in FIG. 4 and described above, may also be made of a combination of metallic and insulating materials provided the specimen is well insulated from the jaw body. Conductive band 503, which provides both good thermal and electrical conduction, contains either one or two heating sections 512 and 512' and functions in the same manner to generate self-inductive and self-resistive heat as do conductors 403 and 403' shown in FIG. 4 and discussed in detail above. As depicted in FIG. 5, one end of band 503 abuts against and electrically contacts end button 610 of specimen 600, while the other end of this band is rigidly secured, by fasteners 526, in tight abutting electrical contact to jaw body 508 and specifically to surface 527 thereof which protrudes into pocket 525. If band 503 is fabricated of material that has essentially the same electrical and thermal resistivity as specimen 600, then the band, if it is formed to contain only one heating section (e.g. section 512), should have approximately the same cross-sectional area as the mid-span region of the specimen in order to prevent essentially any longitudinal thermal gradients from appearing along the entire specimen during heating. Of course, as noted above, the cross-section of band 503 and the material used to fabricate it can be appropriately chosen in order to provide a desired non-zero longitudinal thermal gradient along the specimen. Also, the overall width of the band as well as the length of the legs existing therein can be modified to provide a desired degree of inductive coupling therebetween and self-inductive heating therefrom. Since the band will typically heat to a temperature in excess of the "Curie temperature" for ferritic materials, then, as described above, the band can be either ferrous or non-ferrous. In this regard, austenitic stainless steels and nickel, both of which are non-ferrous, are two suitable materials from which band 503 can be fabricated. If specimen 600 is low carbon steel, then its resistance will be less than stainless steel or nickel which, in turn, will permit band 503 to possess an increased cross-sectional area than that of the specimen.

Inasmuch as band 503 will generate considerable heat, the heat which propagates to surface 527 of jaw body 508 must be conducted away from this surface. Accordingly, jaw body 508 should be water-cooled preferably through use of water passages machined into the jaw body.

Specimen 600 is tightly secured in place through screw jack 511. This jack is threaded into jaw body 508 and is adjusted so hex jack nut 514 forces insulating washer 504 tightly against an end-face of button 610 of the specimen. Inasmuch as the screw jack and hex nut 514 are both metallic, washer 504, which provides good thermal and electrical insulation, prevents both current and heat from flowing through the screw jack. Use of the washer advantageously permits compressive force to be transmitted through the screw jack to the specimen while forcing electrical current to flow through conductive band 503. To extend the life of the jack threads (not specifically shown) in the jaw body, these threads can contain stainless steel helicoil inserts mounted in an aluminum body. Screw jack 511 may be replaced by a suitable pneumatic or hydraulic system. For example, a piston and cylinder may be located in jaw body 508. An end of a piston rod would then protrude through a hole in band 503 and, when properly extended, exert suitable mechanical force on washer 504.

Shaft 519 provides mechanical and electrical connections from the remainder of the dynamic thermal-mechanical testing system to jaw body 508. Cooling water can also be channeled bi-directionally through the shaft to and from the jaw assembly.

As noted above, specimens of differing sizes and shapes and materials can be used with my inventive jaw assemblies. In this regard, FIG. 6 shows an illustrative "button-end" cylindrical test specimen 600, having a circular cross-section, that can be used in conjunction with my inventive jaw assemblies shown in either FIGS. 4 or 5.

Here, specimen 600 is formed by appropriately machining a cylindrically shaped piece of material to produce mid-span region 620 spanned at opposing ends thereof by buttons 610 and 610'. This specimen can be used for both compressive and tensile testing. Each button has a larger cross-sectional area than at its mid-span region. However, to permit a constant heating rate to occur longitudinally throughout the button and the mid-span region, the size of the button (i.e. its diameter and thickness) is chosen such that, if the button were viewed as a washer situated on the end of the specimen with a hole equal in diameter to the specimen diameter, the total inner circumferential surface area of the button would equal the cross-sectional area of the specimen itself (equal at both of its ends and at its mid-span region). As such, if no electrical or thermal current were to flow between the end of the specimen itself and the button, the thermal density that would radially occur from the inner perimeter of the button would equal that which would flow through a cross-section of the specimen itself. If the buttons were to be eliminated and abutting contact established between the ends of the specimen alone and conductors 403 and 403' (as shown in FIG. 3), then the resulting thermal and electrical contact areas to the specimen would likely be too small for use with relatively large sized specimens and particularly for the thermal and electrical currents associated therewith. While experimental tests have indicated that the size of the button is not critical, nevertheless, the button should not either be too small so as to cause excessively high current densities which might cause welding to occur or too large so as to impart excessive thermal mass to the ends of the specimen and conduct excess heat therefrom. In the event, a button were to be too large, then that button would disadvantageously heat at a slower rate than the mid-span region and undesired longitudinal thermal gradients would appear in the specimen. A portion of the mechanical force produced by the testing system is transmitted through friction occurring from the wedge grips to the contact surface of the specimen. This friction is enhanced by jacking the specimen into place, as described above. Accordingly, each button only needs to support the force imparted by each jaw assembly that exceeds the frictional holding force in the wedge grip. Alternatively, the buttons can be replaced by nuts threaded onto the ends of the specimen, though this arrangement is likely to provide thermal and electrical conduction that is inferior to that resulting from use of buttons.

Figure 7:
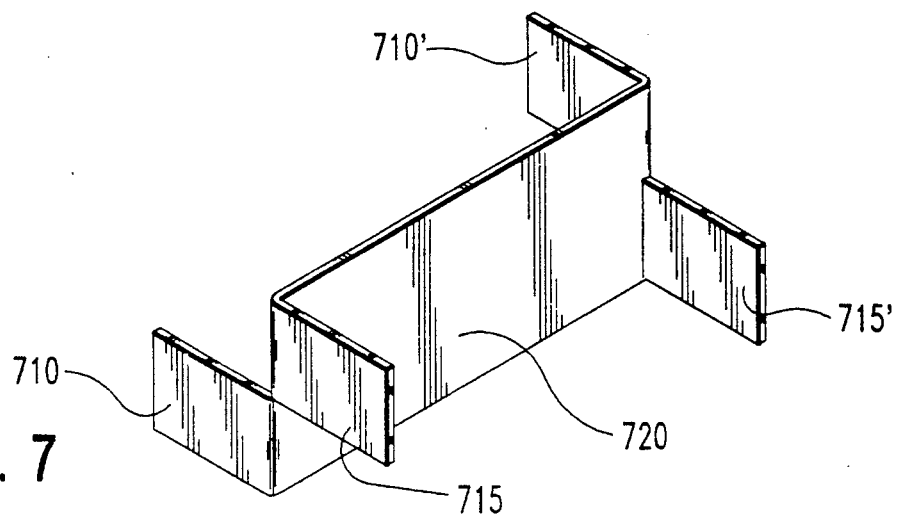
FIG. 7 shows an illustrative "bent-end" sheet metal test specimen, having a rectangular cross-section, that can also be used in conjunction with my inventive jaw assemblies shown in either FIGS. 4 or 5.

FIG. 7 shows an illustrative "bent-end" sheet metal test specimen 700, having a rectangular cross-section, that can also be used in conjunction with my inventive jaw assemblies shown in either FIGS. 4 or 5. This specimen, formed of sheet metal and having a rectangular cross-section, is often used for tensile testing. As shown in FIG. 7, specimen 700 is formed, typically by bending, to contain two bent tabs 710 and 715, and 710' and 715', respectively, at each end thereof. Each pair of these tabs located at an end of the specimen abuttingly contacts the "self-inductive/self-resistive" conductor(s) in a corresponding jaw assembly and establishes good thermal and electrical contact between that jaw assembly and the specimen. While many other specimen shapes are possible, FIGS. 6 and 7 illustrate the two shapes that are expected to be principally used in most dynamic thermal-mechanical material tests.

If, through use of my invention, a uniform temperature is established throughout a specimen that has a mid-span region with a uniform cross-sectional area, then during testing, that specimen can fracture at any point along its length. Well-known standardized procedures, as described above, are generally used to initially form such specimens with slightly reduced mid-span cross-sectional areas such that, during room temperature testing, fractures can be induced to occur along the mid-span region. The amount of any such reduction is governed by specifications for the test specimen that is to be used in a particular test. Inasmuch as my invention advantageously permits a uniform elevated temperature to be established either along the entire length of a specimen or merely along its mid-span region, a similar reduction in mid-span cross-sectional area can also be used with specimens that are to undergo heating in order to control the location of the fracture region therein.

Figure 8:
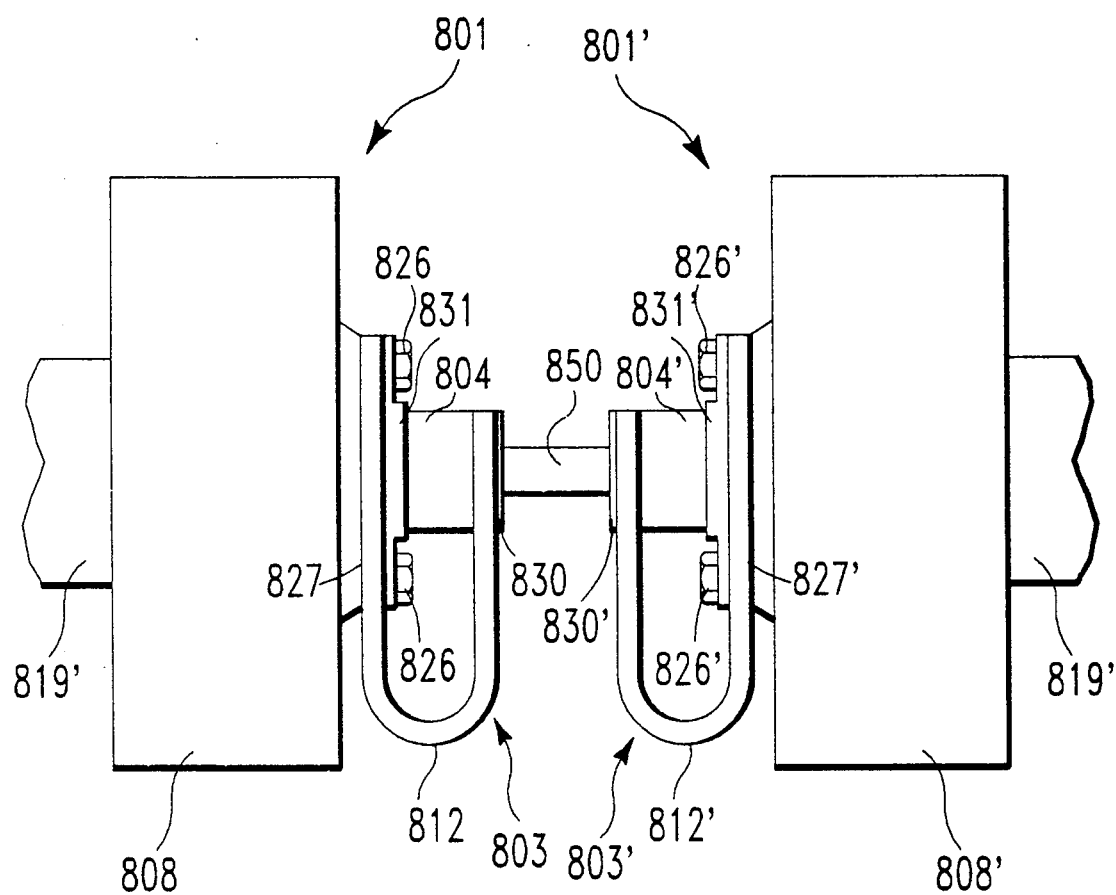
FIG. 8 shows a further embodiment of my inventive jaw assemblies that can be used to compressively test "slug" type specimens.

FIG. 8 shows a further embodiment of my inventive jaw assemblies that can be used for compressively testing "slug" type specimen 850, particularly for hot flow stress testing. A slug specimen is a cylindrical specimen of completely uniform cross-sectional area in which the length of the specimen is usually less than three times the specimen diameter; with the latter typically being on the order of 10 to 12 millimeters. A slug specimen has no buttons on its ends. Here, flat jaws (particularly anvils) rather than wedge grips are used to hold specimen 850, with the specimen being retained between identical jaw assemblies 801 and 801' merely by a compressive force exerted on the specimen by both jaw assemblies. During specimen heating, this compressive force applied by these jaw assemblies is generally just sufficient to reduce the electrical and thermal resistances at the interfaces between each end of the specimen and a corresponding jaw assembly thereby assuring good electrical and thermal flow therebetween. Conductive bands 803 and 803' conduct electric current from jaw bodies 808 and 808' to opposite ends of specimen 850. Both of these conductors are formed to possess an approximately 180 degree bend and provide heating sections 812 and 812' which function in the specific manner described in detail above. One end of conductive bands 803 and 803' is attached at interfaces 827 and 827' to jaw bodies 808 and 808' by fasteners 826 and 826', respectively. These fasteners also secure clamps 831 and 831'. Insulating blocks 804 and 804' (specifically insulating anvils), which are similar to blocks 404 and 404' (see FIG. 4), support the outer ends of conductive bands 803 and 803' in place and are also secured to jaw bodies 808 and 808' by respective fasteners 826 and 826'. These bands may be bent to provide a desired amount of positional friction that holds the outer ends of these bands in place or may be secured by appropriate well-known fasteners (not shown) to the outer surfaces of both insulating blocks. After heating has occurred and during subsequent compression testing, slug specimen 850 increases in cross-sectional area as it decreases in length. As a result of this deformation, sliding occurs at the ends of the specimen. This sliding can disadvantageously cause the specimen ends to stick or weld to conductive bands 803 and/or 803'. To provide appropriate lubrication between the conductive bands and the specimen ends and thereby avoid any such sticking and/or welding, thin sheet 830 and 830' of a suitable material (such as tantalum or carbon, as discussed above) can be situated between each end of specimen 850 and a neighboring conductive band 803 and 803', respectively. Connecting shafts 819 and 819' transmit mechanical compressive forces to jaw bodies 808 and 808' from the remainder of the dynamic thermal-mechanical testing system, carry electrical heating current therefrom to the jaw bodies and also bi-directionally channel cooling water to and from the jaw bodies.

Figure 9:
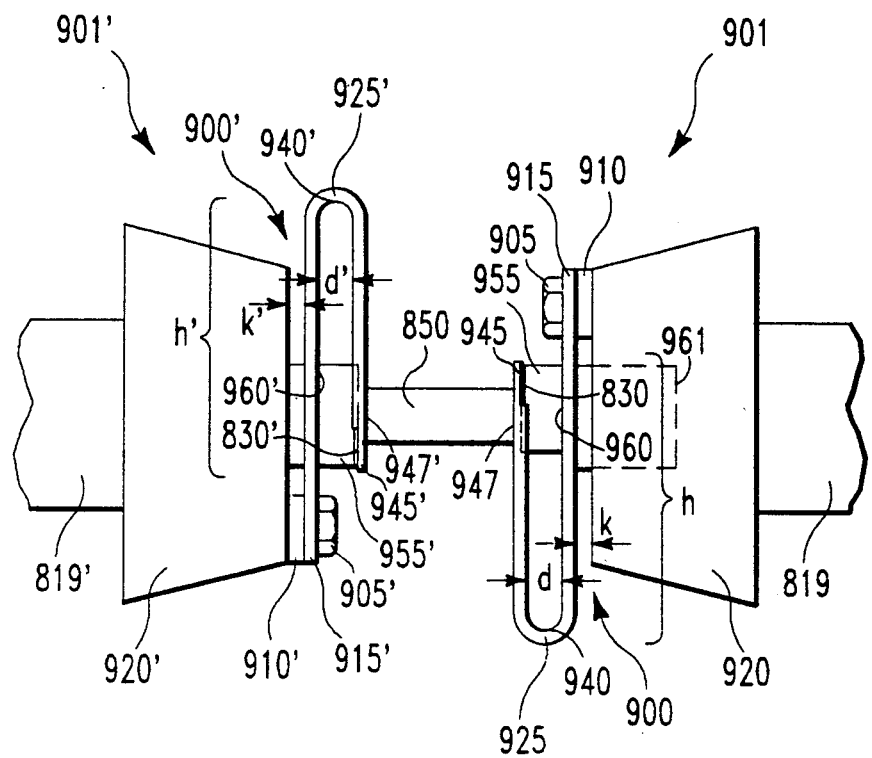
FIG. 9 shows a further embodiment of my inventive jaw assemblies having shaped heating sections for increasing the heat at each end of the specimen.

FIG. 9 shows a further embodiment of my inventive jaw assemblies 901 and 901' that can be used for compressively testing "slug" type specimen 850. In comparison with the jaw assemblies of FIG. 8, jaw assemblies 901 and 901' of FIG. 9 advantageously concentrate heat generated by conductive bands 900 and 900' at specimen contact areas 947 and 947' abutting each end of specimen 850. The main drawback of the jaw assemblies shown in FIG. 8 is their inability to couple current from the portion of band 803 that contacts interface 827 to the portion of the band that contacts an end of specimen 850. Specifically, in jaw assembly 801, current enters heating section 812 via interface 827. The interface couples current to the conductive band along an extensive portion of the band. Since the current at the interface is flowing in a direction perpendicular to the interface, the current is not producing a magnetic field which will couple to the end of the conductive band that abuts the specimen. In this manner, all of the inductive coupling occurs near the bend in the heating section, i.e., where the current flows in opposite but parallel paths. Consequently, the greatest amount of heat is generated where the inductive coupling occurs, i.e., near the bend in the heating section.

My inventive concept moves the location of maximum heating to the end of the specimen to beneficially produce a more efficient heating arrangement. In this manner, decreased current is necessary to produce the same amount of heat at the end of the specimen. To ensure that heat is most efficiently coupled to specimen 850 in FIG. 9, the maximum temperature along conductive bands 900 and 900' must occur at the end of each band which abuts specimen 850. In general, my inventive jaw assemblies use specific design features which optimize the inductive and resistive heating characteristics of each conductive band, such as a contoured band cross-sectional area and an extensive inductive coupling area, to maximize the temperature at each end of the specimen.

Specifically, conductive bolts 905 and 905' respectively attach one end 915 and 915' of conductive bands 900 and 900' to each jaw body 920 and 920'. Spacers 910 and 910' separate conductive bands 900 and 900' from jaw bodies 920 and 920' by respective distances k and k'. Through this arrangement, electrical current serially flows through jaw body 920, conductive band 900, specimen 850, conductive band 900' and jaw body 920'. Both conductive bands possess approximately 180° bends 940 and 940' to form heating sections 925 and 925' which function in the specific manner described in detail above. However, by attaching the bands only at ends 915 and 915' and spacing each band a distance k and k' from each respective jaw body, inductive coupling occurs along length h and h', i.e., where portions (legs) of each and on either side of bends 940 and 940' are parallel. In particular, current is inductively coupled to ends 945 and 945' of each band 900 and 900' where these ends contact specimen 850, i.e., at contact areas 947 and 947'. Thus, the resultant inductive coupling transfers as much heat producing current as possible to the specimen contact area on each band. The amount of this transfer, i.e., the magnitude of the inductive coupling, is governed by spacing d and d' between the parallel portions of each band and length h and h' of each respective parallel portion, as previously described herein.

Insulating blocks 955 and 955' support ends 945 and 945' of conductive bands 900 and 900', respectively. Here, each block 955 and 955' abut respectively, and passes through respective bore holes 960 and 960' to abut each jaw body surface. For increased mechanical stability, each jaw body surface may contain a bore hole (illustratively indicated as dashed line 961) and each block 955 and 955' may extend therein. Additionally, extending the length of the block to interact with a bore hole reduces the thermal gradient along the entire block during high temperature operations. This reduction in the thermal gradient reduces the risk that blocks 955 and 955' will break down under high temperature operation.

During compression testing, the specimen simultaneously increases in cross-sectional area and decreases in length. Thus, the insulating block and the area against which the specimen abuts on the band must be sized to accommodate the increased cross-sectional area of the compressed specimen. Additionally, as a result of this deformation, sliding occurs at the ends of the specimen. As with the previous embodiment shown in FIG. 8, the present embodiment shown in FIG. 9 must be provided with appropriate lubrication between the conductive bands and the specimen ends to avoid sticking and/or welding. Thin sheets 830 and 830' of a suitable material (such as tantalum or carbon, as discussed above) can be situated between each end of specimen 850 and corresponding neighboring conductive bands 900 and 900'. As with the previous embodiment, connecting shafts 819 and 819' transmit mechanical compressive forces to jaw bodies 920 and 920' from the remainder of the dynamic thermal-mechanical system, carry electrical heating current therefrom to the jaw bodies and also bi-directionally channel cooling water to and from the jaw bodies.

Conductive bands 900 and 900' are depicted in an asymmetric orientation, i.e., both having their bent portions on opposite sides of specimen 850. However, this alignment is not necessary for operation of this embodiment. The conductive bands can be positioned in any orientation relative to one another. However, to limit inductive coupling between bands 900 and 900', which can lead to an uncontrolled source of coupling, the bands are preferably asymmetrically oriented.

Additionally, to minimize producing a temperature gradient orthogonal to the direction of current flow through specimen 850, the thermal-mechanical test system should preferably have a balanced magnetic structure, such as that used in the GLEEBLE 2000. Generally, in a test system having an unbalanced magnetic structure, the return path for the current flowing through specimen 850 is located on one side of the specimen. Consequently, such an arrangement produces a magnetic field between specimen 850 and the current return path. This magnetic field produces a lateral temperature gradient in the specimen, wherein the specimen is hottest on the side nearest the current return path. A test system having a balanced magnetic structure eliminates this temperature gradient by having multiple current return paths oriented symmetrically about the specimen. Consequently, the magnetic field generated by each of the symmetric return paths will cancel one another within the specimen. Thus, the magnetic fields do not influence the heating of the specimen and no lateral temperature gradients are produced. For further information on a dynamic thermal-mechanical testing system that utilizes a balanced field, the reader is referred to my co-pending U.S. patent application entitled "A Dynamic Thermal-Mechanical Material Testing System Utilizing a Balanced Magnetic Field", U.S. Ser. No. 07/694,911 filed May 2, 1991 which is also owned by the present assignee hereof.

Figure 10:
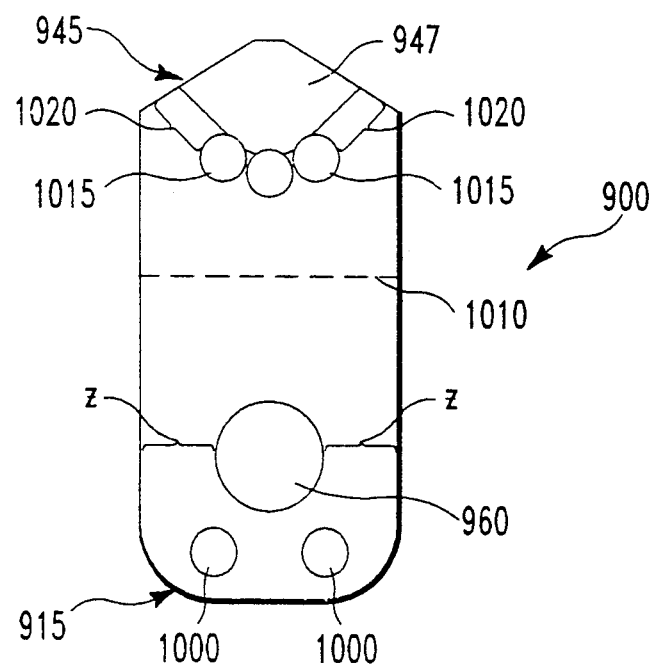
FIG. 10 shows a plan view of shaped conductive band 900 shown in FIG. 9.

FIG. 10 depicts a plan view of band 900 shown in FIG. 9. Mounting holes 1000 located at end 915 interact with bolts 905 and spacers 910 (one of each is shown in FIG. 9) to secure the band to jaw body 920. Hole 960 permits the insulating block to pass through the band and abut the jaw body. Portions of the band that are adjacent hole 960, shown as distance z, must be sufficiently large to permit high current flow through the band to the specimen without melting the band. Dashed line 1010, depicts an approximate bend line, where band 900 is bent to form bend 940 (as shown in FIG. 9).

End 945 of band 900 is shaped (as shown in FIG. 10) to cause preferential resistive heating of the band at specimen contact area 947. A number of holes 1015 remove conductive band material directly above the specimen contact area. By virtue of removing this material, heating current flows through regions 1020 and produces increased heating near specimen contact area 947. Additionally, area 947 is machined to have a smaller cross-sectional area than the remainder of the band. As such, the current density increases at end 945 of band 900. Since heating is proportional to the square of the current density, the temperature of the band near the specimen increases. By appropriately shaping the band and ensuring that inductive coupling occurs at the end of the band which abuts the specimen, the current density and hence the temperature at the specimen contact area can be maximized.

Figure 11:
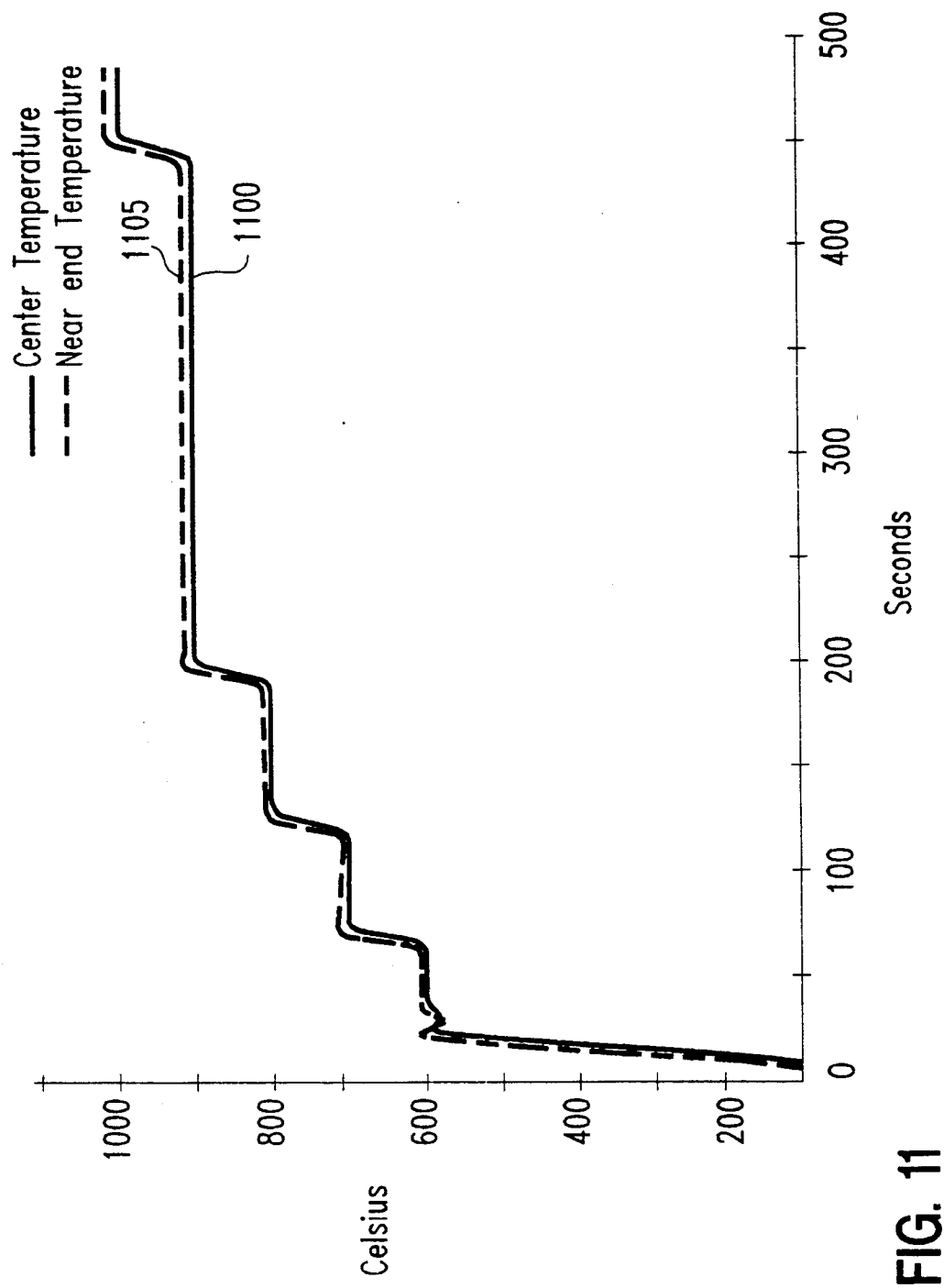
FIG. 11 graphically depicts a thermal gradient that occurs along a specimen heated by jaw assemblies 901 and 901' shown in FIG. 9.
Figure 12:
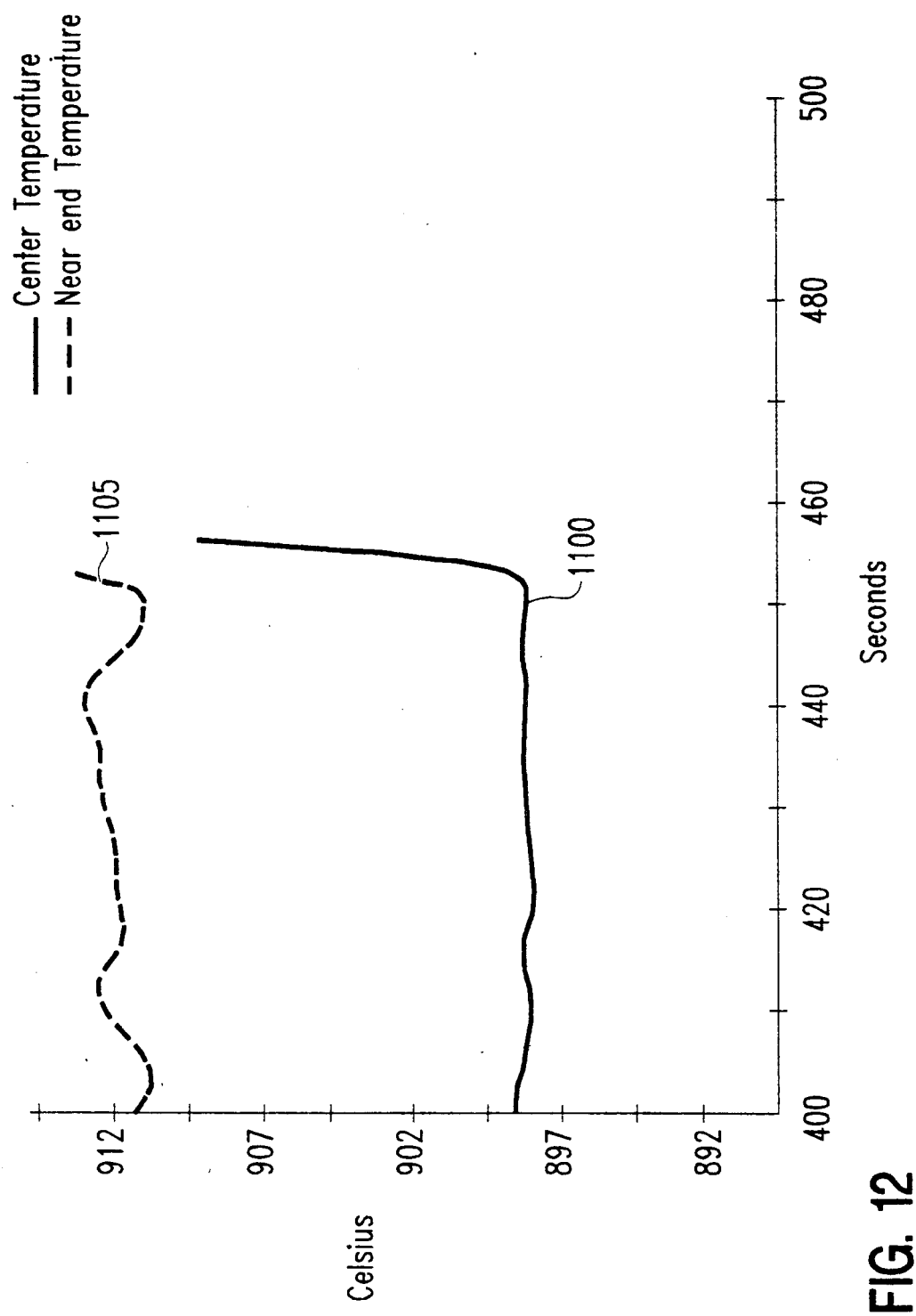
FIG. 12 is an expanded view of a portion of the graph shown in FIG. 11, and specifically for a time period occurring between 400 and 460 seconds after an initial application of heating current to jaw assemblies 901 and 901'.
Figure 13:
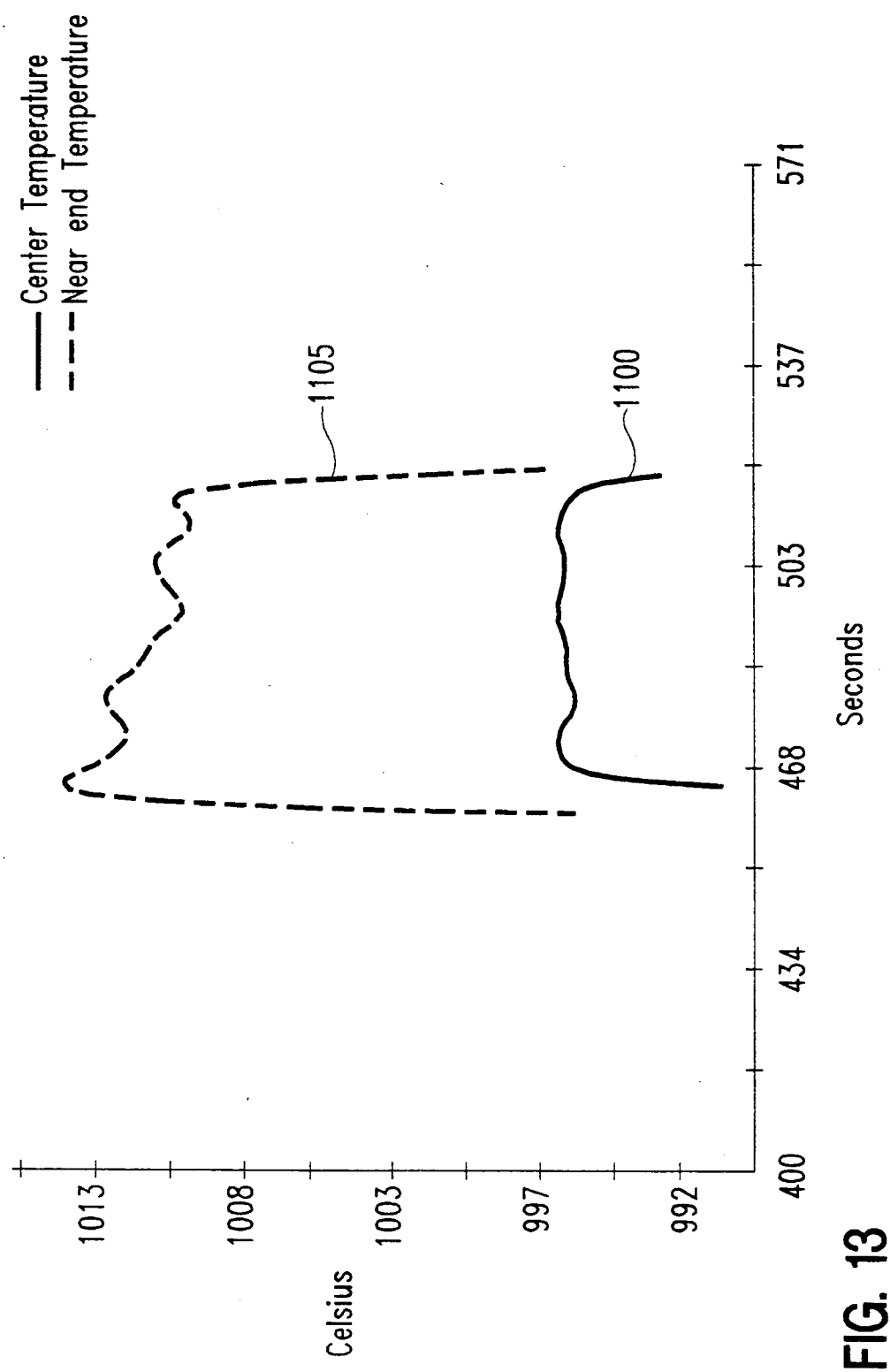
FIG. 13 is an expanded view of another portion of the graph shown in FIG. 11, and specifically for a time period occurring between 468 and 510 seconds after initial current application of heating current to jaw assemblies 901 and 901'.

To illustrate the effectiveness of this embodiment of my invention for heating a test specimen, FIGS. 11, 12 and 13 show graphs 1100 and 1105 of experimental test data acquired while self-resistively/self-inductively heating a test specimen using my inventive jaw assemblies. To best understand the information provided in these figures, FIGS. 11, 12 and 13 should be referred to simultaneously for the following discussion. To acquire the test data, a stainless steel, "slug" type specimen having a 10 mm diameter and a 12 mm length was positioned between the jaws of the embodiment of the invention shown in FIG. 9. The spacing between the jaws was adjusted to apply a sufficient force to ensure good conductive contact between the specimen and the contact area of each conductive band. One thermocouple ("center" thermocouple) was spot welded to the center of the specimen; a second thermocouple ("end" thermocouple) was spot welded to a location on the specimen 1 mm from one end of the specimen. Current was then applied to the specimen via the conductive bands.

As shown in FIG. 11, as the current through the specimen increased over 500 seconds in a stepwise manner, the temperature at the center of the specimen (solid line 1100) tracked but remained slightly less than the temperature occurring near the end of the specimen (dashed line 1105). FIG. 12 shows an expanded view of graphs 1100 and 1105 (shown in FIG. 11) for an interval of time between 400 and 460 seconds after initial application of current to the specimen. In the approximately 900° C. temperature range, the end thermocouple measured a temperature 11° C. higher than the measured center temperature. Similarly, FIG. 13 shows an expanded view of graphs 1100 and 1105 (shown in FIG. 11) for an interval of time between 460 and 520 seconds after initial application of current to the specimen. As shown, when the temperature at the center location of the specimen increased to approximately 1000° C., the temperature near the end of the specimen was 18° C. higher than the temperature at the center of the specimen. In comparison, traditional self-resistive specimen heating systems which do not utilize jaws having self-inductive, self-resistive conductive bands typically heat the center of a specimen to 1000° C. while the temperature at the ends of the specimen is 100 to 120° C. less than the temperature at the center.

As the measured data suggests, by tailoring the self-resistive, self-inductive characteristics of the conductive bands, a temperature gradient along a specimen can be contoured to have the ends of the specimen at a higher temperature than the mid-span region of the specimen. By adjusting the cross-sectional area of the specimen contact area on each conductive band and adjusting the spacing between the parallel portions of the conductive bands, the temperature at the ends of the specimen can be controlled to be higher, lower or the same as the temperature at mid-span of the specimen. Consequently, using conductive bands with differing self-resistive, self-inductive characteristics generates different amounts of heat at each end of the specimen, and produces a controlled thermal contour along the length of the specimen.

Clearly, while my invention has been described in terms of providing two heating sections in the specimen itself or one heating section in each conductor formed within each jaw assembly, any number of such heating sections can be associated with each specimen or conductor, regardless of whether an equal number of such sections is associated with each specimen or conductor. In this regard, more sections can be used at one end of the specimen than the other. In fact, one end can have no such sections associated therewith, while the other end has one or more such sections associated therewith. The number and/or location(s) of all of these sections on the specimen itself or the number of such sections located within each jaw assembly will be governed by the desired thermal gradient, if any, that is to be longitudinally established throughout the specimen.

One drawback of the foregoing embodiments is their inability to heat non-conductive material specimens such as ceramics and composites. Clearly, the previous embodiments relied upon passing current through a specimen to force it to undergo self-resistive heating. However, ceramic and composite materials typically do not conduct current nor exhibit self-resistive heating. Thus, in accordance with my inventive teachings the foregoing embodiments are modified to permit specimens of ceramic and composite materials to be mechanically tested under thermal and thermal gradient stress.

Figure 14:
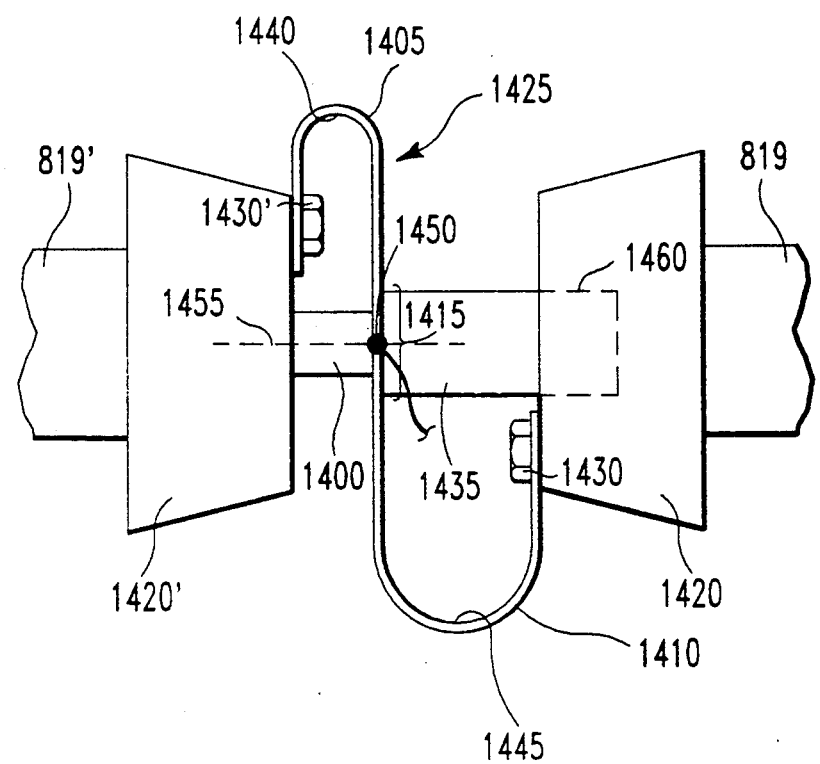
FIG. 14 shows another embodiment of my inventive jaw assemblies that can be used for establishing a thermal gradient along a non-conductive specimen.

FIG. 14 depicts an embodiment of my invention for producing a thermal gradient across non-conductive "slug" type specimen 1400. In general, specimen 1400 mounts between conductive band 1425 and jaw body 1420'. By passing current through conductive band 1425, the band heats which, in turn, heats one end of specimen 1400. The other end of specimen 1400 abuts jaw body 1420' and remains cool due to liquid cooling of the jaw body. By precisely controlling the current through conductive band 1425, the amount of heat the band generates and applies to one end of specimen is accurately controlled. Thus, the invention produces a temperature difference between conductive band 1400 and jaw body 1420', which, in turn, produces a thermal gradient across specimen 1400.

Specifically, conductive band 1425 possesses two approximately 180° bends 1440 and 1445 which collectively form an S-shaped conductive band. Each end of the conductive band connects to a face of jaw bodies 1420 or 1420' by conductive bolts 1430 or 1430', respectively. Thus, conductive band 1425 provides a conductive path for AC electrical current flowing between jaw body 1420 and jaw body 1420'. The curved portions of conductive band 1425 form heating sections 1410 and 1405 which function in the specific manner described in detail above. Insulating block 1435 provides support for central section 1415. Block 1435 abuts central section 1415 at one end and abuts the jaw body face at the other end. For increased mechanical stability, each jaw body surface may contain a bore hole (illustratively shown as dashed line 1460) and block 1435 may extend therein. Extending the length of the block also reduces the thermal gradient along the block during high temperature operations. Typically, block 1435 is constructed of a ceramic insulating material.

Importantly, the ends of S-shaped conductive band 1425 must not overlap the center line of the specimen (shown as dashed line 1455). Such overlap would cause the magnetic fields generated by each end of the conductive band to cancel within central section 1415. Detrimentally, any canceled magnetic fields reduces the self-inductive heating component and, consequently, reduces the amount of heat generated at central section 1415.

Figure 15:
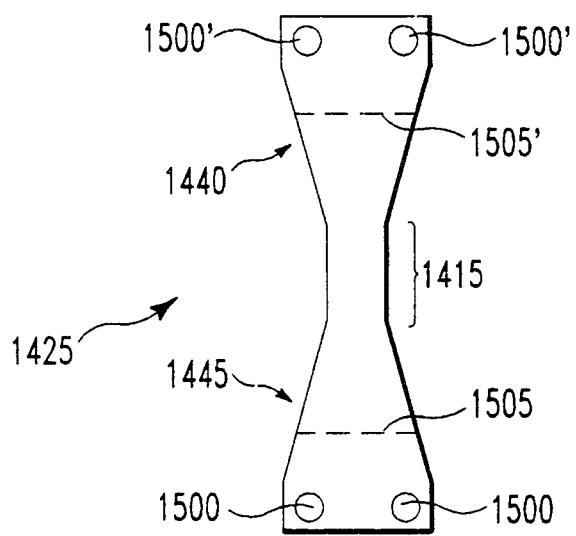
FIG. 15 shows a flat plan view of heating conductive band 1425 shown in FIG. 14.

FIG. 15 depicts a plan view of band 1425. Mounting holes 1500 and 1500' located at each end of band 1425 interact with bolts 1430 and 1430' (shown in FIG. 11). The bolts secure the band to each jaw body. Each 180° bend 1440 and 1445 in band 1425 occurs along dashed lines 1505 and 1505', respectively. To provide a desired increase in temperature at central section 1415, the cross-sectional area of the central section is reduced in size as compared to the remainder of band 1425. This reduced central section increases the current density through the center of the band and, thus, increases the temperature within the area. As such, the central section becomes the hottest portion of band 1425.

Returning to FIG. 14, thermal-couple 1450 is spot welded to central section 1415 to monitor the temperature of the central section. The thermal-couple produces an electrical signal indicative of the temperature of one end of the specimen. Typically, the electrical signal from the thermal-couple will be used by the GLEEBLE system, either the GLEEBLE 1500 or 2000, to monitor and control the temperature at one end of the specimen and, thus, the thermal gradient produced along the length of the specimen. Using the GLEEBLE system as a temperature control system, any desired temperatures versus-time profile in the specimen can be generated. Additionally, by adjusting the length of specimen 1400, i.e., altering the distance between central section 1415 and the surface of jaw body 1420', any desired thermal gradient slope, i.e., temperature vs. distance, can be imposed across specimen 1400. Additionally, as previously discussed with respect to the heating sections of the previous embodiment, the physical characteristics of heating sections 1405 and 1410, i.e., size and shape, can be altered to produce various desired thermal gradients along the length of the specimen.

As with the previous embodiments, connecting shafts 819 and 819' transmit mechanical compressive forces to jaw bodies 1420 and 1420' from the remainder of the dynamic thermal-mechanical system, carry electrical heating current therefrom to the jaw bodies and also bi-directionally channel cooling water to and from the jaw bodies.

Figure 16:
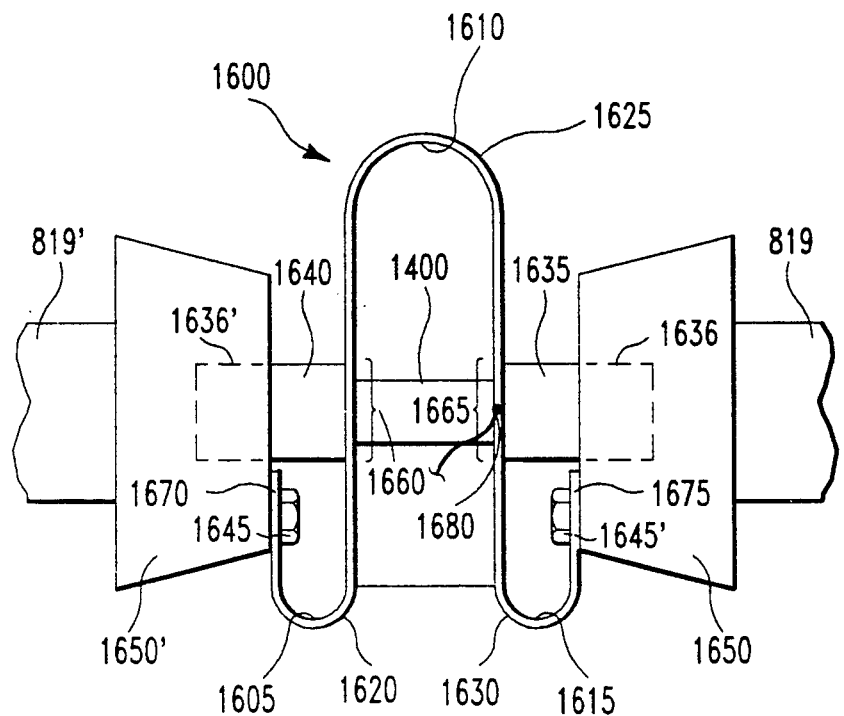
FIG. 16 shows a further embodiment of my inventive jaw assemblies that can be used for heating non-conductive specimens.

FIG. 16 shows a further embodiment of my inventive jaw assemblies that can be used for compressively testing non-conductive "slug" type specimen 1400. In general, conductive band 1600 is provided to conduct electric current between jaw bodies 1650 and 1650'. Self-conductive and self-resistive characteristics of band 1600 cause the band to heat in a similar manner as previously discussed with respect to the heating sections of the previous embodiments. As such, heat generated by band 1600 conducts into each end of specimen 1400 and, consequently, heats the specimen. Generally speaking, this embodiment permits heating of the specimen such that a thermal gradient is not formed along the length of the specimen, i.e., so-called uniform heating. In comparison, the embodiment shown in FIG. 15 is designed to produce a thermal gradient along the length of the specimen.

Specifically in FIG. 16, conductive band 1600 possesses three approximately 180° bends, 1605, 1610 and 1615, each forming heating sections 1620, 1625 and 1630, respectively. Working central sections 1660 and 1665 abut each end of specimen 1400 and conduct heat thereto. Insulating blocks 1635 and 1640 supported each working section 1660 and 1665, respectively. Each insulating block 1640 and 1635 abuts the surface of jaw body 1650' and 1650, respectively. For increased mechanical stability, each jaw surface may contain a bore hole (illustratively shown as dashed line 1636 and 1636') and each block 1635 and 1640 may extend therein. Extending the length of each block reduces the thermal gradient along the blocks during high temperature operation. Each end 1670 and 1675 of conductive band 1600 attaches to respective jaw body 1650 and 1650' by bolts 1645 and 1645'. As such, current flows between jaw body 1650 and jaw body 1650' via conductive band 1600. During current flow, heating sections 1620, 1625 and 1630 function in the specific manner previously described in detail in conjunction with the other embodiments of this invention. Consequently, self-inductive and self-resistive heating heats working sections 1660 and 1665 which, in turn, heat the ends of specimen 1400.

Figure 17:
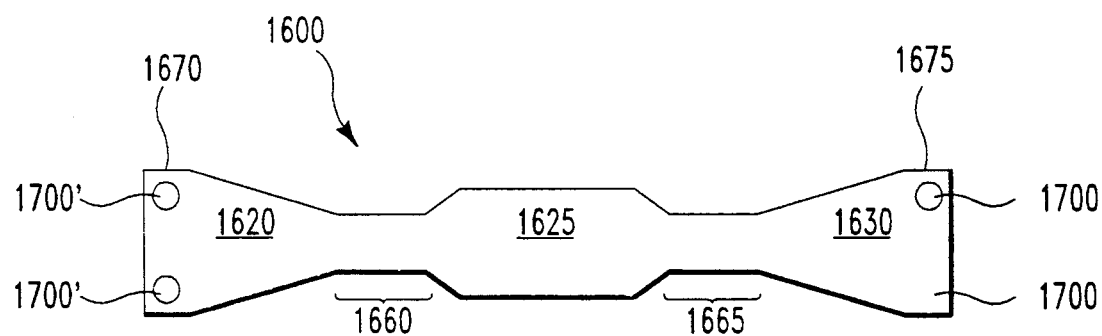
FIG. 17 shows a flat plan view of heating conductive band 1600 shown in FIG. 16.

FIG. 17 depicts a plan view of band 1600 shown in FIG. 16. Mounting holes 1700 and 1700' located at ends 1670 and 1675 interact with bolts 1645 and 1645' (shown in FIG. 16). The bolts secure each end of the band to each jaw body, respectively. To increase the temperature at working sections 1660 and 1665 when compared to the remainder of band 1600, working sections 1660 and 1665 have reduced cross-sectional areas in comparison to the cross-sectional areas of heating sections 1620, 1625, and 1630. The reduced cross-sectional areas of working sections 1660 and 1665 increases the current density through each working section and, consequently, increases the heat generated at the ends of specimen 1400 by each working section.

Importantly, the cross-sectional areas of working sections 1660 and 1665 do not have to be equivalent. If they are equivalent and the length and width of the heating sections are also equivalent, then typically, the temperature gradient across the specimen is substantially zero. However, to generate a thermal gradient across the specimen, working sections 1660 and 1665 can have differing cross-sectional areas and, consequently, generate different amounts of heat at each end of the specimen. Additionally, as with the previous embodiments of my invention, the physical dimensions of the heating sections, i.e., length and width, can be varied to produce a thermal gradient across the specimen.

Returning to FIG. 16, a thermal-couple 1680, located on working section 1680, can be provided to monitor the temperature of one or both of the working sections. Using an electric signal produced by the thermal-couple as an input to the GLEEBLE system, enables an accurate computer controlled thermal profile to be generated across specimen 1400.

Using the embodiment of the invention shown in FIG. 16, a thermal gradient between two very high temperatures may be generated across a non-conductive specimen. Typically, using stainless steel as the conductive band material, the temperature at the working sections is on the order of 1000 to 1300° C. However, by using tantalum as the conductive band material and placing the embodiment in a vacuum, the temperature of one or both working sections may reach 2500° C.

As with the previous embodiments, connecting shafts 819 and 819' transmit mechanical compressive forces to jaw bodies 1650 and 1650' from the remainder of the dynamic thermal-mechanical system, carry electrical heating current therefrom to the jaw bodies and also bi-directionally channel cooling water to and from the jaw bodies.

The foregoing embodiments of the invention operate exclusively by conducting heat to each end of a specimen. The following embodiment of the invention is capable of heating conductive as well as non-conductive specimens without passing current through the specimen and without physically contacting the specimen.

Figure 18:
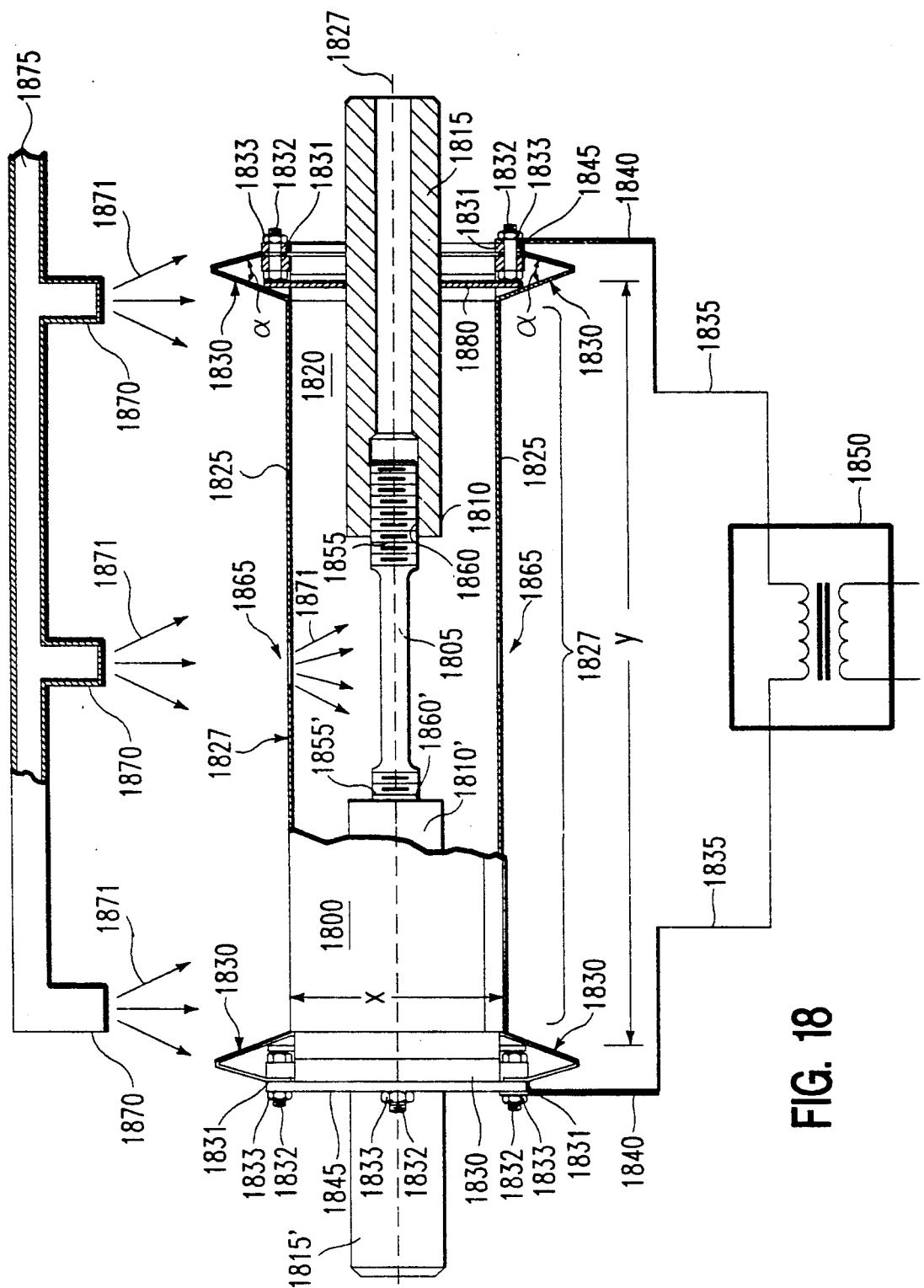
FIG. 18 shows oven 1800, formed in accordance with my inventive teachings, which experiences both self-resistive and self-inductive heating.
Figure 19:
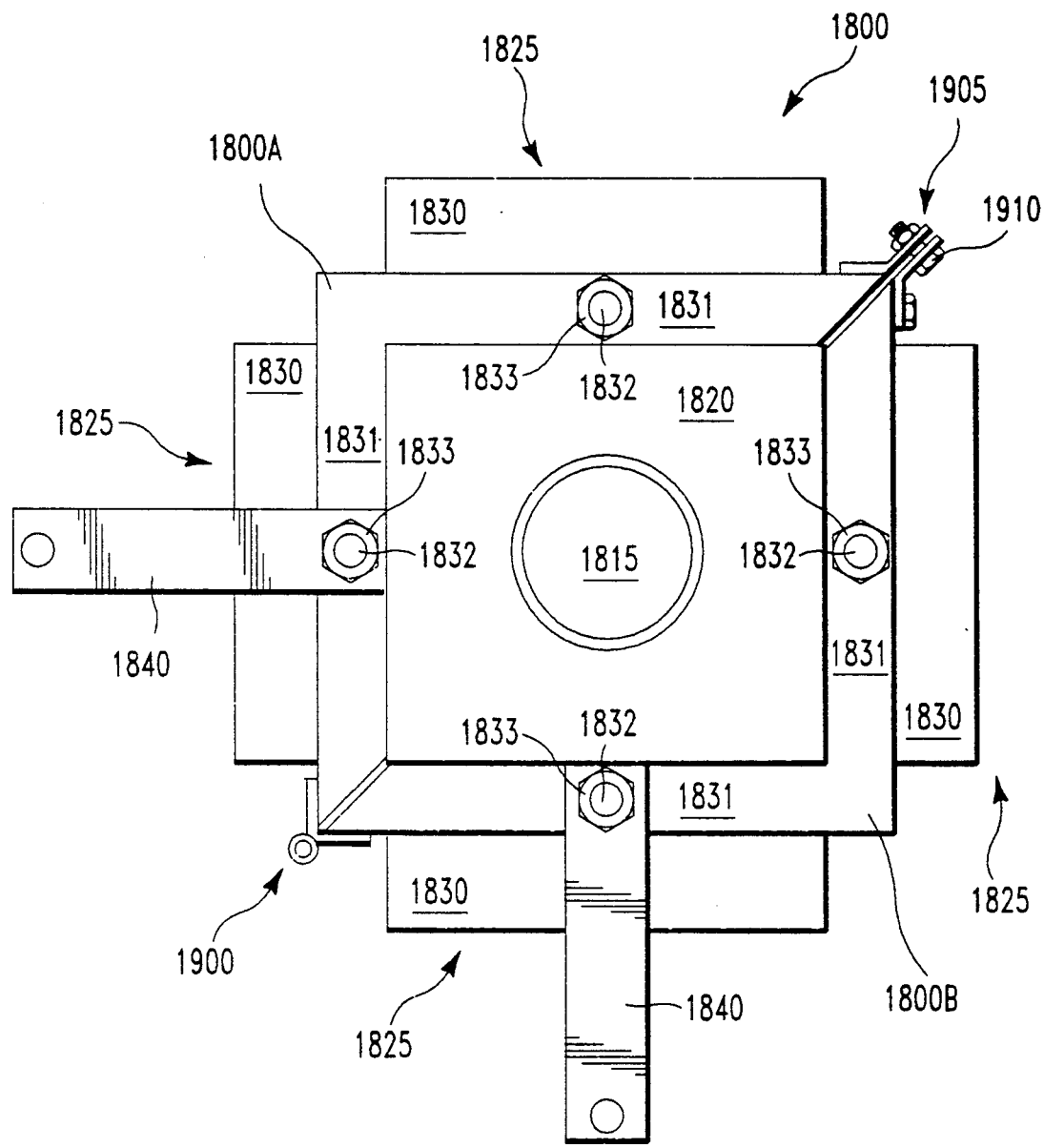
FIG. 19 shows an end view of oven 1800 shown in FIG. 18.

FIGS. 18 and 19 depict self-inductive/self-resistive (SI/SR) oven 1800 constructed in accordance with the teachings of my invention. Specifically, FIG. 18 depicts a side-sectional view of SI/SR oven 1800 and FIG. 19 depicts an end perspective view of that oven. The reader should refer to both of these figures for the following discussion. Generally, through both self-inductive and self-resistive heating of the oven walls, oven 1800 radiantly heats a material specimen placed therein. In this regard, the oven walls 1825 define an internal volume wherein the specimen is positioned.

Specifically, extension shafts 1810 and 1810' support each end of specimen 1805. The extension shafts are attached by distal ends 1815 and 1815' to jaws of a GLEEBLE system machine (not shown, for simplicity) or a conventional mechanical testing machine that imparts torsion, tensile and/or compressive forces upon a specimen. Shafts 1810 and 1810' centrally position specimen 1805 in SI/SR oven 1800. To generate heat in SI/SR oven 1800, AC current is passed through oven walls 1825. To ensure controlled heating of sidewalls 1825, heating sections 1830, which function in an identical manner to those described above with reference to FIG. 3, are incorporated into each end of each sidewall 1825. Consequently, by virtue of these sections, each sidewall of SI/SR oven 1800 heats uniformly along its length. As such, specimen 1805 heats along its length. Each of these heating sections may be triangular, U, or rectangularly shaped.

More specifically, each sidewall 1825 of SI/SR oven 1800, depicted in FIG. 18, comprises mid-span region 1827 having a rectangular plan form. In addition, each sidewall includes a heating section 1830 located at each end of mid-span region 1827. Four sidewalls 1825 are arranged to form a rectangular volume that defines internal volume 1820 of the oven. To achieve uniform heating of volume 1820, the four sidewalls should each have a width (x) smaller than a length (y) of the mid-span region. Longitudinal axis 1827 of the internal volume is aligned with an axis of specimen 1805. In use, the oven mounts to a fixed support (not shown) by mounting flange 1831 attached to each heating section 1830. Bolts 1832 and nuts 1833 secure flange 1831 to the support. Flexible electrical leads 1835 connect to electrical busses 1840 and supply electrical current, via clamps 1845 and 1845', to heating sections 1830. Alternatively, an arrangement of cam locs, one per mounting flange, secure each mounting flange to a conductive support. The conductive support supplies electric current directly to the heating sections.

Transformer 1850 supplies AC electrical power to leads 1835. The transformer is a low-voltage/high current type as used in the GLEEBLE system. To accurately control the temperature of the oven, a thermo-couple and control electronics (not shown) can be used to control the current applied to the oven.

In operation, leads 1835 connect a high current secondary winding of transformer 1850 to SI/SR oven 1800. The high current flows from one end of the oven to the other. As previously discussed with respect to FIG. 3, triangular-shaped heating sections 1830 generate heat through the self-inductance and self-resistance of each section. Additionally, mid-span region 1827 self-resistively heats as the current flows therethrough. Consequently, the mid-span region radiantly heats the specimen while the triangular-shaped heating sections compensate for any heat lost to the oven mounting assembly and extension shafts supporting the specimen. To adjust the amount of compensatory heating that is generated, the angle ($\alpha$) of each triangular-shaped heating section can be altered in the manner previously described above. Alternatively, if the heating sections are "hat" or rectangular-shaped, altering the height and distance of separation of the legs of each heating section adjusts the amount of self-inductive heat produced thereby. As a result of properly shaping the heating sections to fully compensate for heat loss, the oven maintains a uniform temperature within the inner volume and hence produces a uniform temperature along the specimen.

FIG. 19 depicts an end perspective view of SI/SR oven 1800. To permit access to internal volume 1820 of SI/SR oven 1800, the oven is constructed in two parts, 1800A and 1800B. One edge of SI/SR oven 1800 contains hinge 1900; clamp 1905 is located on an edge diagonally opposite this hinge. The clamp is secured in a "closed" position by bolt and nut combination 1910. The hinge and clamp retain the oven in its rectangular, box-like shape during use. Access to the internal volume of the oven is provided by disengaging clamp 1905, i.e., by removing bolt and nut combination 1910, and moving either half 1800A or 1800B of the oven to an open position (not shown). In operation, the specimen is first placed in the testing system and the oven is physically installed around specimen. Lastly, the oven, once closed around the specimen is connected to the conductive supports.

As depicted in FIG. 18, to best control convection heat loss out of the open ends of the oven, a sheet of aluminum-oxide ($Al_2O_3$) insulation 1880 (only one such sheet is shown) is positioned at each end of the oven. Each such sheet extends into the heating sections and circumscribes each extension shaft 1810 or 1810'. Alternatively, the sheets of insulation can be replaced with an insulating wool. The selection of the type of insulation depends upon the temperature that is expected to be generated by the oven during a particular test situation.

Importantly, the SI/SR oven can achieve very high temperatures within its internal volume in a very short duration. For example, an oven with sidewalls of approximate dimensions of 50 millimeters width by 20 millimeters length and a thickness of 1 millimeter, can achieve heating rates of hundreds of degrees per second. Moreover, by using austenitic stainless steel as the oven material, the oven can operate at temperatures up to 1200° C.

To facilitate imparting mechanical stresses upon specimen 1805, the specimen is threaded on both ends 1855 and 1855'. The threaded ends of the specimen are screwed into threaded bores 1860 and 1860' (as shown in FIG. 18) in extension shafts 1810 and 1810', respectively. Since the ends of the oven are open (aside from insulating sheets), extension shafts 1810 and 1810' can move freely in and out of internal volume 1820. Therefore, the jaws of the GLEEBLE system (not shown) or a conventional mechanical test system can impart compressive, torsion and tensile forces upon the specimen while it is being heated in SI/SR oven 1800. Additionally, because current is not passed through the specimen, the specimen can be a conductive material, such as copper, aluminum, or steel, as well as a non-conductive material, such as ceramic, glass, composite, or a polymer. Some specimen materials may not be amenable to having threaded ends. In these instances, conventional clamping-type jaws or a collet could be extended into the oven to grasp and apply the appropriate forces to the specimen.

Advantageously, my inventive oven has a low thermal mass which enables the oven to be heated and cooled very quickly. In many applications, it is necessary to cool a specimen very rapidly using a liquid coolant such as water or a gas coolant such as nitrogen. Typically, a conventional oven having high thermal mass retains heat after the specimen is cooled and imparts the retained heat to the specimen which, in turn, causes the temperature of the specimen to rise thereby potentially corrupting ensuing test results. In contrast, due to its low thermal mass, the heat retained by my inventive oven is very small. Thus, using coolant to quench both the specimen and the oven simultaneously, cools both the specimen and oven rapidly. Consequently, specimen re-heating is not possible since the oven retains substantially no heat. To facilitate quenching of the specimen, sidewalls 1825 contain one or more holes 1865 to permit entry into the inner volume of a high pressure coolant, such as water. Spray nozzles 1870 and coolant conduit 1875 provides coolant 1871 (from a supply not shown) to the oven and specimen. Typically, each side of the oven is associated with a plurality of nozzles 1870. However, to simplify FIG. 18, only one set of three nozzles is shown.

Certain specimen testing regimens may require maintaining a particular thermal gradient along the length of the specimen. The physical shape of the heating sections can be altered to generate various heating characteristics and thus generate nearly any desired thermal gradient along the length of the oven. Particularly, the inductive coupling in the triangular-shaped heating sections can be adjusted by changing the angle ($\alpha$) between the legs comprising each section. By altering the heating sections so that the inductive coupling at each end differs, the heat generated at the ends of the mid-span region produces a thermal gradient along the mid-span region, i.e., more heat is produced at one end of the region than the other. Similarly, if "hat" or rectangular-shaped heating sections are used, the length and separation of the heating section legs at each end of the oven can be altered to produce a thermal gradient along the length of the oven. Additionally, the width of the heating sections themselves can be changed to alter the self-resistive heating characteristic of each section and, consequently, alter the heat generated at the ends of the mid-span region. Alternatively, the inductive and resistive heating characteristics of the various sections can be altered to be non-symmetric about the central axis of the oven; thereby, causing uneven heating of the specimen, if so desired.

One particular application, i.e., in vertically oriented mechanical testing machines, necessitates the use of a thermal gradient along the mid-span region of the SI/SR oven to compensate for an unwanted thermal gradient in a specimen. If a specimen is contained in a vertically oriented conventional oven during testing, the heat produced by the oven rises and heats an upper end of the specimen more than the lower end producing an undesired thermal gradient. However, my inventive oven can be advantageously used to compensate for the undesired thermal gradient and, thus, uniformly heat a vertically oriented specimen. To do so, the heating sections of the SI/SR oven can be altered to heat the upper end of the oven less than the lower end so as to compensate for the rising heat. Consequently, the specimen heats without producing a thermal gradient.

The embodiment of the SI/SR oven shown in FIGS. 18 and 19 is depicted as having four sides. Alternatively, ovens with more than 4 sides will function equally as well, if not better. For example, each half of the oven could be constructed to have three or four sides making the overall oven have six or eight sidewalls. A six or eight-sided oven, though more difficult to manufacture, heats a specimen more uniformly than a four-sided oven. More uniform heating occurs because, in an eight-sided oven, the distance from the specimen to a center of a side is relatively equal to the distance from the specimen to a corner. Therefore, the radiant heat from the sidewalls of an eight-sided oven propagates substantially the same distance from the corner as from the side and, consequently, uniformly heats the specimen about its circumference. Also, for optimal uniformity in wall-to-specimen distance, the oven could be constructed as a cylinder. As such, the heating sections at the ends are formed by cutting serrations in the ends of the cylinder and folding each serration into a heating section of a desired shape and size.

Although various embodiments which incorporate the teachings of my present invention have been shown and described in detail herein, those skilled in the art can readily devise many other varied embodiments that still incorporate these teachings.

I claim:

1. An oven for providing controlled heating, wherein said heating occurs in response to an alternating current flowing through the oven, said oven comprising:
   a plurality of sides, each having a mid-span region which collectively form a cavity centrally located between opposing ends of the oven, each of said sides contain a conductive material capable of being self-resistively heated and having eddy current flow induced therein; and a heating section formed in each of said sides at a location intermediate said mid-span region and at least one of said ends, wherein said heating section has a pre-defined shape and size such that said section undergoes self-induction in response to flow of the alternating current through each of said sides and generates both self-inductive and self-resistive heat therein which, in conjunction with self-resistive heat generated in the mid-span region of each of said sides by said current, establishes a pre-defined temperature within said cavity.

2. The oven in claim 1 wherein said oven comprises two heating sections in each side, wherein each one of said heating sections is situated intermediate said mid-span region and a different corresponding one of said ends.

3. The oven in claim 2 wherein said oven further comprises means for holding a testing specimen within the oven and coaxially along a longitudinal axis thereof and centrally located within the oven.

4. The oven in claim 3 wherein said alternating current occurs at power line frequencies.

5. The oven in claim 4 wherein said material is a conductive ferrous or non-ferrous material.

6. The oven in claim 5 wherein each of said heating sections is fabricated into a substantially U shape with respect to a longitudinal axis of the oven.

7. The oven in claim 5 wherein each of said heating sections is fabricated into a substantially rectangular shape with respect to a longitudinal axis of the oven.

8. The oven in claim 5 wherein each of said heating sections is fabricated into a substantially triangular shape with respect to a longitudinal axis of the oven.

9. The oven in claim 5 wherein each of said heating sections is formed by bending said side into said pre-defined shape.

10. The oven in claim 5 wherein said sides of said mid-span region define holes through which a coolant may flow into said cavity.

11. A method of heating an oven that is formed of a conductive material capable of being self-resistively heated and having eddy current flow induced therein and having a plurality of sides, each having a mid-span region which collectively define a cavity centrally located between opposing ends of the oven and a heating section formed in the sides at a location intermediate said mid-span region and at least one of said ends, wherein said heating section has a pre-defined shape and size such that said section undergoes self-induction in response to flow of the alternating current through each of said sides and generates both self-inductive and self-resistive heat therein, said method comprising the steps of:

controllably passing alternating current through said heating sections so as to generate self-inductive and self-resistive heat within said oven which, in conjunction with self-resistive heat generated in the mid-span region of each of said sides by said current; and producing a pre-defined temperature within said cavity to controllably heat a specimen contained therein.

12. The method in claim 11 further comprising the step of forming two heating sections in each side of said oven, wherein each side of said oven includes one of said sections situated intermediate said mid-span region and a different corresponding one of said ends.

13. The method in claim 12 wherein said alternating current occurs at power line frequencies.

14. The method in claim 13 wherein said material is a conductive ferrous or non-ferrous material.

15. The method in claim 14 wherein said forming step comprises the step of fabricating each heating section into a substantially U shape with respect to a longitudinal axis of the oven.

16. The oven in claim 14 wherein said forming step comprises the step of fabricating each heating section into a substantially rectangular shape with respect to a longitudinal axis of the oven.

17. The oven in claim 14 wherein said forming step comprises the step of fabricating each heating section into a substantially triangular shape with respect to a longitudinal axis of the oven.

18. The oven in claim 14 wherein the forming step further comprises the step of forming each of said heating sections by bending said side of said oven into said pre-defined shape.

* * * * *